United States Patent
Lashinsky et al.

(10) Patent No.: US 11,872,345 B2
(45) Date of Patent: Jan. 16, 2024

(54) PATIENT SLEEP THERAPY MASK SELECTION TOOL

(71) Applicant: KONINKLIJKE PHILIPS N.V., Eindhoven (NL)

(72) Inventors: Michael Lashinsky, Monroeville, PA (US); Melissa Sue Ross, Monroeville, PA (US); Ryan T. Kasun, Monroeville, PA (US); Kevin Anthony Coldren, Monroeville, PA (US); Richard Andrew Sofranko, Finleyville, PA (US); Jonathan Sayer Grashow, Pittsburgh, PA (US); Robert William Baiko, Pittsburgh, PA (US); Daniel Steed, North Huntingdon, PA (US); Praveen Kumar Pandian Shanmuganathan, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 366 days.

(21) Appl. No.: 16/893,841

(22) Filed: Jun. 5, 2020

(65) Prior Publication Data
US 2020/0384229 A1 Dec. 10, 2020

Related U.S. Application Data

(60) Provisional application No. 62/858,365, filed on Jun. 7, 2019.

(51) Int. Cl.
*G06F 3/0484* (2022.01)
*A61M 16/06* (2006.01)

(52) U.S. Cl.
CPC ....... *A61M 16/0605* (2014.02); *G06F 3/0484* (2013.01); *A61M 2016/0661* (2013.01); *A61M 2205/583* (2013.01)

(58) Field of Classification Search
CPC .......... G06F 3/0484; A61M 2205/583; A61M 2016/0661; A61M 16/0605
See application file for complete search history.

(56) References Cited

U.S. PATENT DOCUMENTS

7,827,038 B2 * 11/2010 Richard ................ A61M 16/06
705/2
9,361,411 B2 * 6/2016 Thiruvengada ......... G06T 19/20
(Continued)

FOREIGN PATENT DOCUMENTS

WO WO-2014075797 A1 * 5/2014 .......... A61M 11/065
WO WO-2015138242 A1 * 9/2015 ........ A61M 16/0605
(Continued)

OTHER PUBLICATIONS

Metamason, "3D Printed Mask: a uniquely fitting device for every patient", retrieved on Aug. 31, 2017 from https://www.metamason.com/3dmask (Year: 2017).*
(Continued)

*Primary Examiner* — Shourjo Dasgupta
(74) *Attorney, Agent, or Firm* — Michael W. Haas

(57) ABSTRACT

A method of identifying a particular mask for a patient for use in delivering a flow of breathing gas to the patient includes capturing with a visual presentation and interaction component a plurality of images of the patient; receiving with the visual presentation and interaction component a number of responses from the patient to questions presented to the patient, eliminating one or more masks from a pool of potential masks for the patent based on at least one of the responses, utilizing at least some images of the plurality of images to determine the particular mask for the patient from the pool of potential masks, and identifying the particular mask to the patient.

19 Claims, 39 Drawing Sheets

(56) References Cited

U.S. PATENT DOCUMENTS

| | | | | |
|---|---|---|---|---|
| 10,114,901 B2* | 10/2018 | Mitrovic | | G06F 16/9535 |
| 10,178,318 B1* | 1/2019 | Marason | | G06T 7/90 |
| 10,664,903 B1* | 5/2020 | Haitani | | G06F 21/31 |
| 2006/0023228 A1* | 2/2006 | Geng | | A61B 5/411 |
| | | | | 356/601 |
| 2006/0235877 A1* | 10/2006 | Richard | | A61M 16/06 |
| 2007/0130020 A1* | 6/2007 | Paolini | | G06Q 30/0643 |
| | | | | 705/26.62 |
| 2008/0060652 A1* | 3/2008 | Selvarajan | | A61M 16/0683 |
| | | | | 128/206.21 |
| 2009/0276291 A1* | 11/2009 | Wannier | | G06Q 30/0631 |
| | | | | 705/26.1 |
| 2011/0220112 A1* | 9/2011 | Connor | | A61M 16/06 |
| | | | | 128/206.24 |
| 2012/0114249 A1* | 5/2012 | Conwell | | G06T 3/00 |
| | | | | 382/190 |
| 2012/0123674 A1* | 5/2012 | Perks | | G06Q 30/0631 |
| | | | | 705/26.7 |
| 2014/0156645 A1* | 6/2014 | Brust | | G06F 3/0481 |
| | | | | 707/722 |
| 2015/0306330 A1* | 10/2015 | Richard | | A61B 5/4818 |
| | | | | 348/77 |
| 2016/0057246 A1* | 2/2016 | Krishnaiahsetty | | G06Q 20/24 |
| | | | | 709/204 |
| 2016/0148437 A1* | 5/2016 | Vlutters | | G06F 3/04815 |
| | | | | 382/128 |
| 2017/0236182 A1* | 8/2017 | Ignatyev | | G06Q 30/0631 |
| | | | | 705/26.7 |
| 2019/0122262 A1* | 4/2019 | Huang | | G06K 19/06037 |
| 2019/0188476 A1* | 6/2019 | Sundaresan | | G06V 20/20 |
| 2020/0160615 A1* | 5/2020 | Jang | | G06T 19/20 |

FOREIGN PATENT DOCUMENTS

| | | | | |
|---|---|---|---|---|
| WO | WO-2015195303 A1 * | 12/2015 | | A62B 23/025 |
| WO | WO-2016000040 A1 * | 1/2016 | | A61B 5/107 |
| WO | WO-2017205903 A1 * | 12/2017 | | G02C 13/003 |

OTHER PUBLICATIONS

International Search Report for PCT/EP2020/065622 dated Jun. 5, 2020.

* cited by examiner

FIG. 14

Mask selector

1 Create — ⊘ Scan — ⊘ Survey — ⊘ Suggestions — ⊘ Mask resources

Create patient

Scan date:
5/7/2019  [15] — 162

Date of birth: (optional)
Select a date  [15] — 164

First name:
Hg Ihgvjyg — 166

Last name:
Hvvuhg Jhg Jhg — 168

Is this a compliant patient?
No   Yes — 171

Patient ID: (optional)
— 170

Next — 172

Mask selector

① Create — ② Scan — ③ Survey — ● Suggestions — ● Mask resources

Patient Survey Questions

Question: 3/9
Does your mask give you irritating soreness or redness on any of the following areas?

[Bridge of nose] [In or around nostrils] [Forehead] [Other areas]
[Not typically bothered by soreness or redness]

Question: 4/9
How happy are you with your current mask?

[Unhappy] [Neutral] [Happy]

Question: 5/9
What is your preffered sleeping position?

[Lying on Back] [Lying on Side] [Lying on Stomach] [Sitting Upright]

Processing facial geometry . . .

Calculating mask recommendations . . .

PATIENT SLEEP THERAPY MASK SELECTION TOOL

CROSS-REFERENCE TO RELATED APPLICATIONS

This patent application claims the priority benefit under 35 U.S.C. § 119(e) of U.S. Provisional Application No. 62/858,365, filed on Jun. 7, 2019, the contents of which are herein incorporated by reference.

BACKGROUND OF THE INVENTION

1. Field of the Invention

The present invention relates to systems for treating conditions, such as sleep disordered breathing, using positive airway pressure (PAP) therapy, and in particular, to a tool configured to, among other things, provide a recommendation of a customized/personalized mask type/model and sizing particulars thereof for a particular patient.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of a patient. The mask component may be, without limitation, a nasal mask that covers the patient's nose, a nasal cradle that interfaces under a patient's nose, a nasal pillows mask that interfaces with the individual nostrils of a patient, a nasal/oral mask that covers the patient's nose and mouth, or a full face mask that covers the patient's face. Such patient interface devices may also employ other patient contacting components, such as forehead supports, cheek pads, chin pads, silicone frames, and headgear elements. The patient interface device is connected to a gas delivery tube or conduit and interfaces the pressure support device with the airway of the patient, so that a flow of breathing gas can be delivered from the pressure/flow generating device to the airway of the patient.

The mask selection process in today's global market is more of an art than a science. In most cases, a sleep professional is involved in the mask selection and sizing. These professionals typically have paper or plastic sizing tools such as gauges provided by the manufacturer, but have limited to no guidance how to choose the proper mask for the patient. Additionally, such sizing tools are generally only applicable to fitting rather coarse sizing arrangements and are generally not useful in sizing more finely sized mask arrangements. Clinicians commonly base their mask selections on their experience with different types of patients and feedback from their peers. It is a trial and error process that often leads to clinician bias for their "go-to" or favorite masks. It is an individual process, so it is not uncommon for clinicians in the same organization to have a widely different selection process and favorite masks. Getting the right mask the first time is key for both the sleep lab and the health care provider (HCP). Sleep labs are dealing with increased pressure to comply with new cleaning standards and more sleep labs are going to single use only masks. At the HCP, the RT has 90 days to get the patient compliant and if the mask does not work the first time they are forced to spend more time and resources getting the patient to accept and comply with therapy. It would thus be advantageous to provide, and there is thus a need for, a system and/or tool that provides for a more scientific, consistent method for identifying and providing the best mask for a given patient the first time.

SUMMARY OF THE INVENTION

Embodiments of the present invention offer a more defined, scientific approach for identifying and providing a mask for a particular patient than those presently employed. In one embodiment, a method of identifying a particular mask for a patient for use in delivering a flow of breathing gas to the patient is provided. The method comprises: capturing, with a visual presentation and interaction component, a plurality of images of the patient; receiving, with the visual presentation and interaction component, a number of responses from the patient to questions presented to the patient; eliminating one or more masks from a pool of potential masks for the patent based on at least one of the responses; utilizing at least some images of the plurality of images to determine the particular mask for the patient from the pool of potential masks; and identifying the particular mask to the patient.

The plurality of images may be captured while someone other than the patient is operating the visual presentation and interaction component.

The plurality of images may be captured while the patient is operating the visual presentation and interaction component.

The visual presentation and interaction component may comprise a tablet PC or a smartphone.

The method may further comprise displaying the plurality of images in an image display area on a display of the visual presentation and interaction component as the plurality of images are captured. The method may further comprise displaying an indicator in the image display area for assisting in positioning the patient in the plurality of images. Displaying the indicator may further comprise displaying the indicator in different colors to provide different indications to a person using the visual presentation and interaction component while capturing the plurality of images. Displaying the indicator may further comprise displaying a directional indicator instructing a person using the visual presentation and interaction component while capturing the plurality of images to move one of the visual presentation and interaction component in a particular direction of for the patient to move in a particular direction.

Identifying the mask to the patient may comprise displaying information regarding the particular mask on a display of the visual presentation and interaction component. The information may comprise a name and size of the particular mask or one or more components of the particular mask. Identifying the mask to the patient may further comprise displaying a 3D model of the head of the patient on the display along with a 3D model of the particular mask disposed on the 3D model of the head.

In another embodiment, a system configured to identify a particular mask for a patient for use in delivering a flow of breathing gas to the patient is provided. The system comprises: a visual presentation and interaction component including a display; and a processor apparatus including a processor and a memory, the memory storing one or more routines executable by the processor, the one or more routines being adapted to: capture, with the visual presentation and interaction component, a plurality of images of the patient; receive, with the visual presentation and interaction component, a number of responses from the patient to questions presented to the patient via the display; eliminate one or more masks from a pool of potential masks for the patent based on at least one of the responses; utilize at least some images of the plurality of images to determine the particular mask for the patient from the pool of potential masks; and identify the particular mask to the patient via the display.

The visual presentation and interaction component may comprise a tablet PC or a smartphone.

The one or more routines may further be adapted to display the plurality of images in an image display area on the display of the visual presentation and interaction component as the plurality of images are captured.

In yet another embodiment, a non-transitory computer readable medium storing one or more programs, including instructions, which when executed by a computer, causes the computer to perform a method of identifying a particular mask for a patient for use in delivering a flow of breathing gas to the patient is provided. The method comprises: capturing with a visual presentation and interaction component a plurality of images of the patient; receiving with the visual presentation and interaction component a number of responses from the patient to questions presented to the patient; eliminating one or more masks from a pool of potential masks for the patent based on at least one of the responses; utilizing at least some images of the plurality of images to determine the particular mask for the patient from the pool of potential masks; and identifying the particular mask to the patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 5-44 are schematic diagrams showing a number of "screen shots" of a touchscreen display of the portable electronic device of FIGS. 1, 3 and 4 that demonstrate the operation and functionality of the software application/tool of the present invention.

DETAILED DESCRIPTION OF EXEMPLARY EMBODIMENTS

Figure 1:
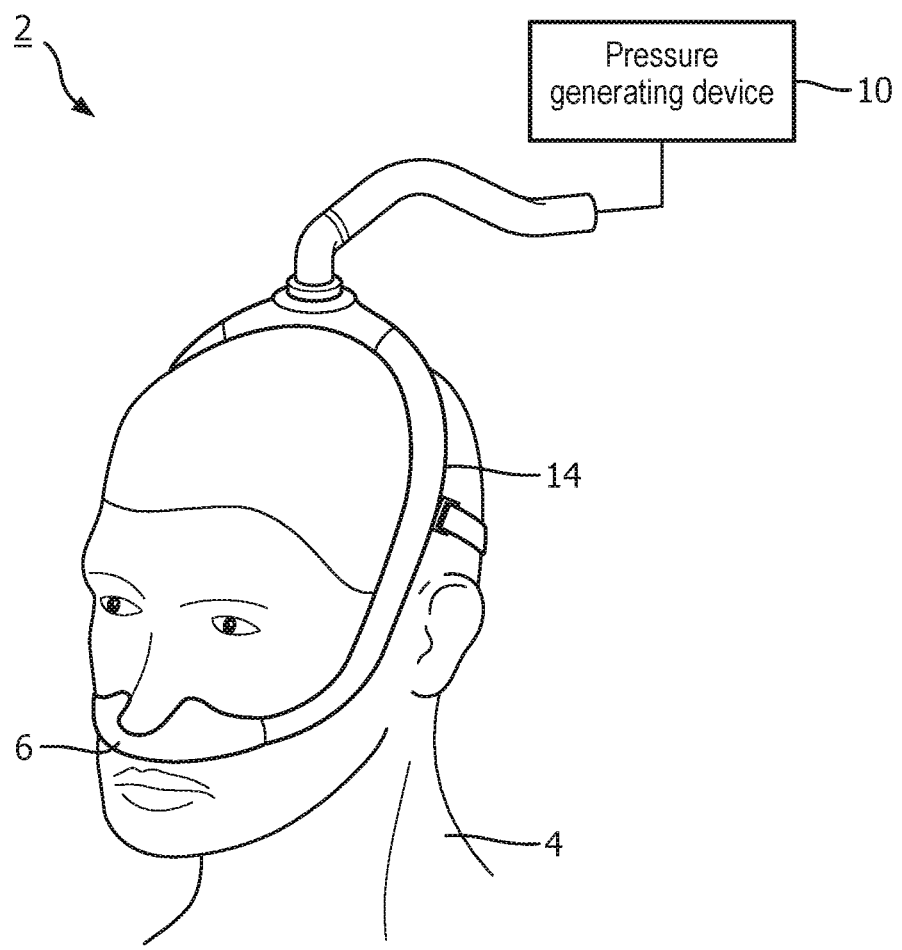
FIG. 1 is a schematic diagram of a known pressure support system for use in delivering a pressurized flow of breathing gas to the airway of a patient.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic diagram of a pressure support system 2 for use in providing a flow of treatment gas to the airway of a patient 4 in which a mask 6, determined for patient 4 using a tool, in the form of a software application, that is implemented using a system 8 (FIG. 2) in accordance with one example embodiment of the present invention, may be employed. Pressure support system 2 includes a pressure generating device 10, a delivery conduit 12, a tubing assembly 14, and mask 6 fluidly coupled to pressure generating device 10 via delivery conduit 12 and tubing assembly 14. Pressure generating device 4 is structured to generate a flow of positive pressure breathing gas and may include, without limitation, ventilators, constant pressure support devices (such as a continuous positive airway pressure device, or a CPAP device), variable pressure devices (e.g., BiPAP®, Bi-Flex®, or C-Flex™ devices manufactured and distributed by Philips Respironics of Murrysville, PA), and auto-titration pressure support devices. Delivery conduit 12 is structured to communicate the flow of breathing gas from pressure generating device 4 to mask 6 through tubing assembly 14 (the breathing gas enters at the top of the head of patient 4). Delivery conduit 12, tubing assembly 14 and mask 6 are often collectively referred to as a patient circuit.

In the example embodiment shown in FIG. 1 mask 6 is a nasal cushion made of a soft, flexible material, such as, without limitation, silicone, an appropriately soft thermoplastic elastomer, a closed cell foam, or any combination of such materials. However, it is to be appreciated that the software application/tool, described in further detail below, may be used to identify any type of mask (e.g., a nasal mask, a nasal cradle mask, a nasal pillows mask, a nasal/oral mask, or a full face mask that covers the patient's face) that facilitates the delivery of the flow of breathing gas to the airway of a patient without varying from the scope of the present invention.

Figure 2:
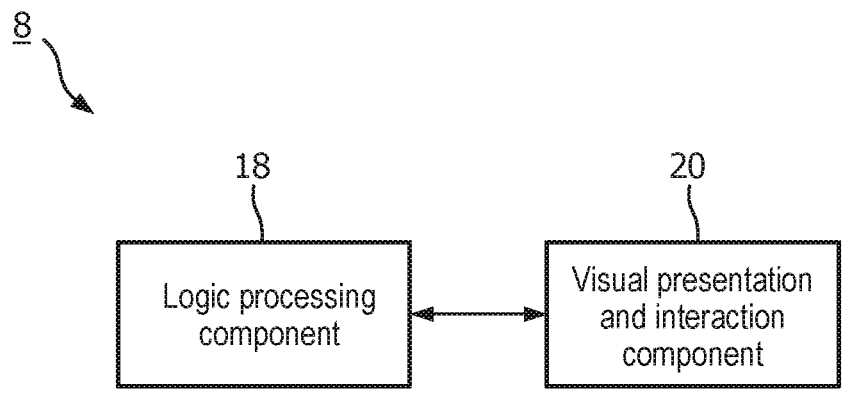
FIG. 2 is a block diagram of a system for identifying a particular mask for a patient for use in a pressure support system such as shown in FIG. 1 according to one non-limiting exemplary embodiment of the present invention.

As previously mentioned, the present invention provides a tool or system, in the form of a software application, that is used for identifying a mask for a particular patient, such as mask 6 for patient 4 as shown in FIG. 1. A block diagram of one example of a system 8 through which such tool may be implemented is shown in FIG. 2. System 8 includes a number of components that, as described in greater detail herein, together provide for a scientific method for identifying/selecting a particular mask and appropriate sizing thereof for a particular patient. More particularly, system 8 includes a Logic Processing Component 18 and a Visual Presentation and Interaction Component 20. In an example embodiment of the present invention, Logic Processing Component 18 is a cloud-based computing platform comprising one or more cloud based databases and one or more webservices associated therewith that carry out particular operations related to the data and provide solutions to particular problems related to identifying and providing a mask for a particular patient. Such arrangement performs services including, but not limited to: registering/logging in clinicians and/or users, processing and analyzing 3D facial models, retrieving and analyzing quizzes, evaluating the best fitting mask sizes, and morphing 3D mask representations to fit 3D models of the patient. Visual Presentation and Interaction Component 20 is a device such as, without limitation, a tablet PC, a smartphone, or some other computing device. One suitable example of a Visual Presentation and Interaction Component 20 that may be used in system 8 is described in detail herein in connection with FIGS. 3 and 4.

Figure 3:
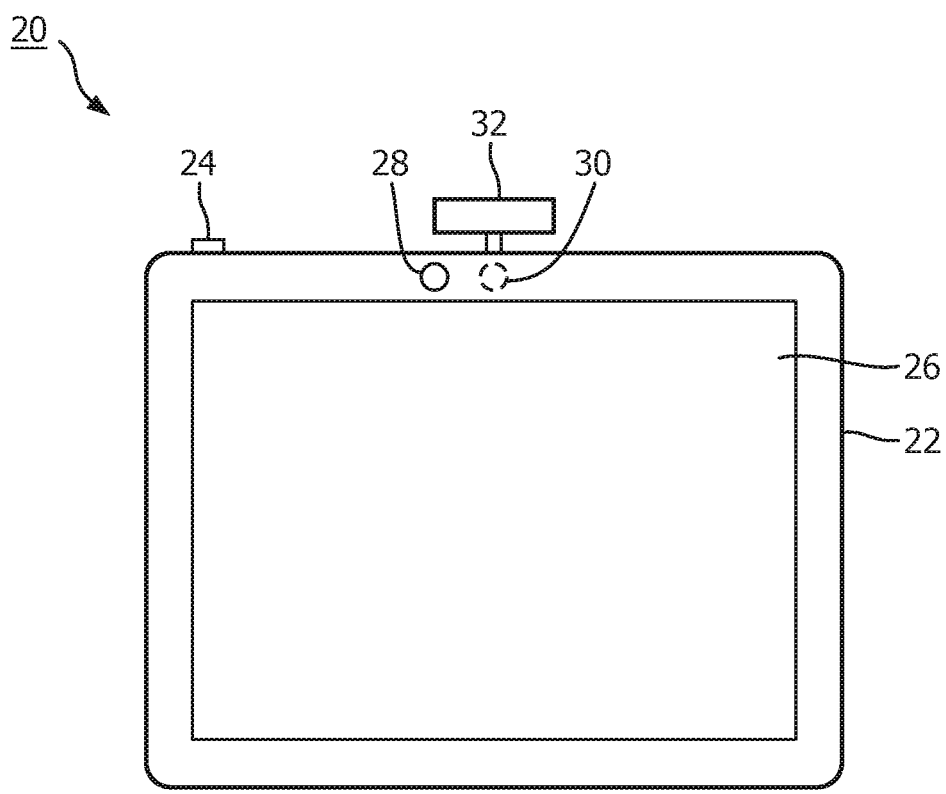
FIGS. 3 and 4 are schematic diagrams of an exemplary portable electronic device that may be used in implementing the system of FIG. 2.

For ease of illustration, one example embodiment of a tool in accordance with one example of the present invention will be described as implemented using an exemplary Visual Presentation and Interaction Component 20 that is indicated generally in FIG. 3 and is depicted schematically in FIG. 4. The exemplary Visual Presentation and Interaction Component 20 is a tablet PC and includes a housing 22, an input apparatus 24 (which in the illustrated embodiment is a button), a touchscreen display 26, at least one of a forward facing camera 28 or a rearward facing camera 30, a depth camera 32, and a processor apparatus 34 (FIG. 4) disposed in housing 22. A user is able to provide input into processor apparatus 34 using input apparatus 24 and touchscreen display 26. Processor apparatus 34 provides output signals to touchscreen display 26 to enable touchscreen display 26 to display information to the user as described in detail herein.

Processor apparatus 34 comprises a processor 36, a fixed disk storage device 37, and a memory module 38. Processor 36 may be, for example and without limitation, a microprocessor (µP) that interfaces with memory module 38. Memory module 38 can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. Fixed disk storage device 37 has stored therein a number of routines that are executable by processor 36. One or more of the routines implement (by way of computer/processor executable instructions) the software application/tool discussed briefly above and described in greater detail below that is configured to, among other things, provide the a customized/personalized mask to the patient based, at least in part, on data that is obtained via Visual Presentation and Interaction Component 20. In one example embodiment, software application/tool, labeled 41 in FIG. 4 for ease of reference, may be downloaded to Visual Presentation and Interaction Component 20 from any suitable source, such as an online "app store." In another example embodiment, only a portion of software application/tool 41 may exist on Visual Presentation and Interaction Component 20 with the remainder elsewhere (e.g., on the cloud). In yet another example embodiment, all of software application/tool 41 exists elsewhere (e.g., on the cloud) and Visual Presentation and Interaction Component 20 is only used to interact therewith.

Figure 4:
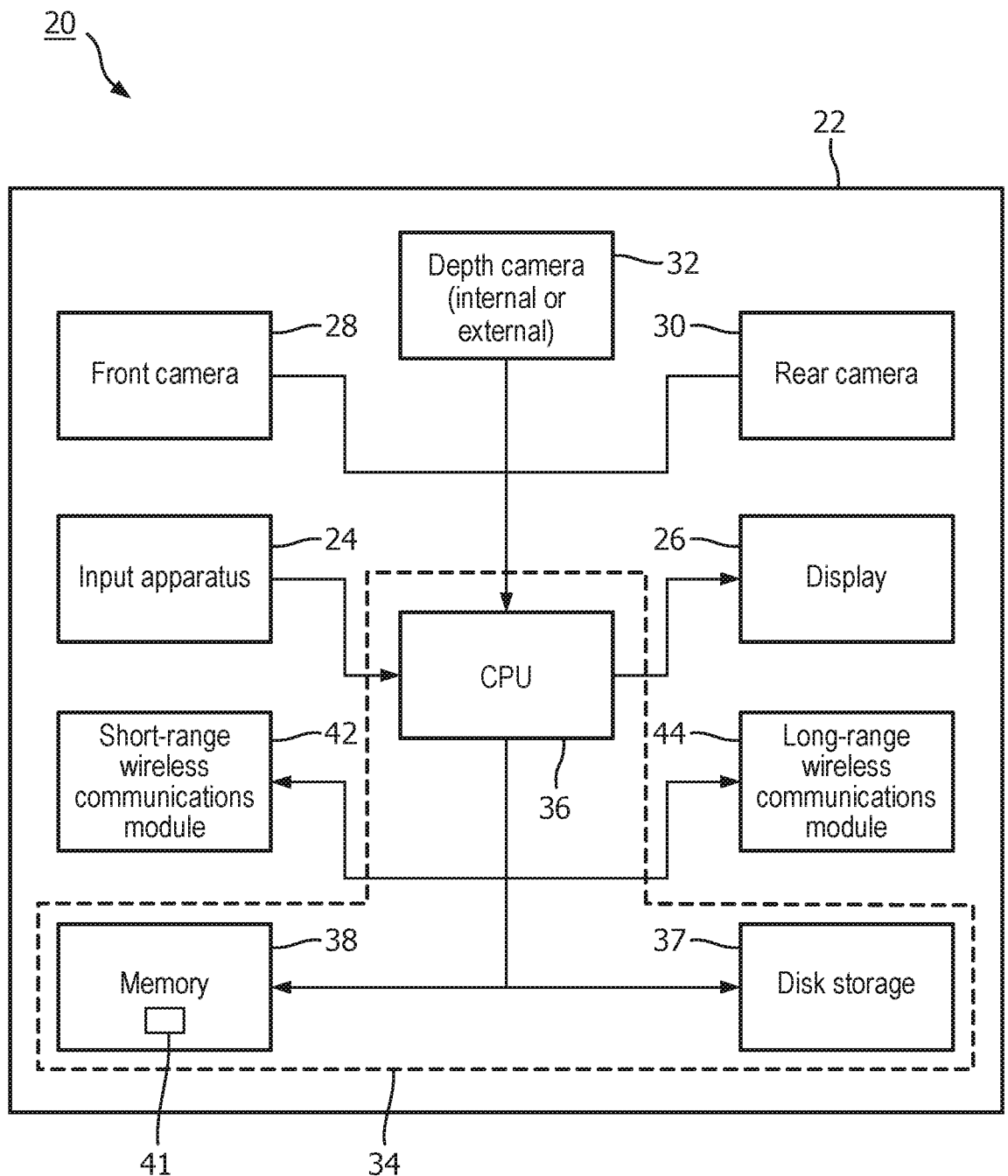

As seen in FIG. 4, Visual Presentation and Interaction Component 20 also includes a short range wireless communications module 42 that is structured and configured to enable Visual Presentation and Interaction Component 20 to communicate with other, similarly equipped electronic devices, over a short range wireless network (e.g., without limitation, Bluetooth). Visual Presentation and Interaction Component 20 also includes a long range wireless communications module 44 (e.g., a wireless networking card) that is structured and configured to enable Visual Presentation and Interaction Component 20 to communicate with Logic Processing Component 18 over a suitable network, such as the Internet. In the exemplary embodiment, Visual Presentation and Interaction Component 20 communicates wirelessly with Logic Processing Component 18, although a wired connection is also possible as is intra process communication should the Logic Processing Component 18 reside on the same physical device as Visual Presentation and Interaction Component 20. In addition, Visual Presentation and Interaction Component 20 may also include one or more additional modules/components that provide additional functionality. For example, and without limitation, Visual Presentation and Interaction Component 20 may include other I/O components, such as, without limitation, a microphone, a speaker and/or other audio I/O components for use in playing videos as described herein or providing other features.

As noted above, system 8, and Visual Presentation and Interaction Component 20 thereof, implements software application/tool 41 that is configured to, among other things, collect facial scans of a patient, construct a 3D model of the patient from such scans, collect information regarding preferences of the patient, use the preferences to narrow a selection of masks to a smaller selection of masks, map three dimensional representations of the masks from the smaller selection of masks to the 3D model, provide 3D images of the smaller selection of masks on the 3D model of the patient, and provide a ranked listing of the suggested masks to the patient. As described in greater detail herein, software application/tool 41 utilizes certain patient metrics captured by one or more of cameras 28, 30, 32, along with further patient information obtained via responses provided by a patient to questions provided by software application/tool 41.

The operation and functionality of software application/tool 41 according to one exemplary embodiment will now be described in detail. In the following description, that operation and functionality will be described in conjunction with a number of "screen shots" of touchscreen display 26 of Visual Presentation and Interaction Component 20 which each comprise a state of touchscreen display 26 as determined by software application/tool 41.

Figure 5:
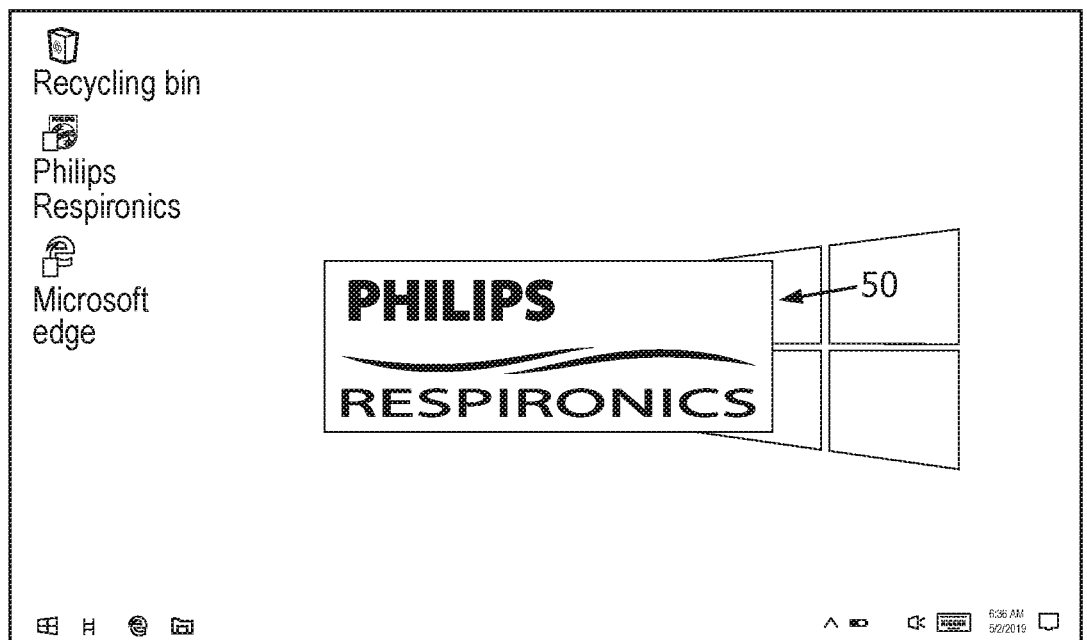

FIG. 5 is a schematic representation of a splash screen 50 that is presented on touchscreen display 26 whenever a user (e.g., a clinician in a sleep lab, a provider of durable medical equipment (DME)) launches software application/tool 41. Such splash screen 50 appears for a brief period of time (e.g., a few seconds) while software application tool 41 initializes.

Figure 6:
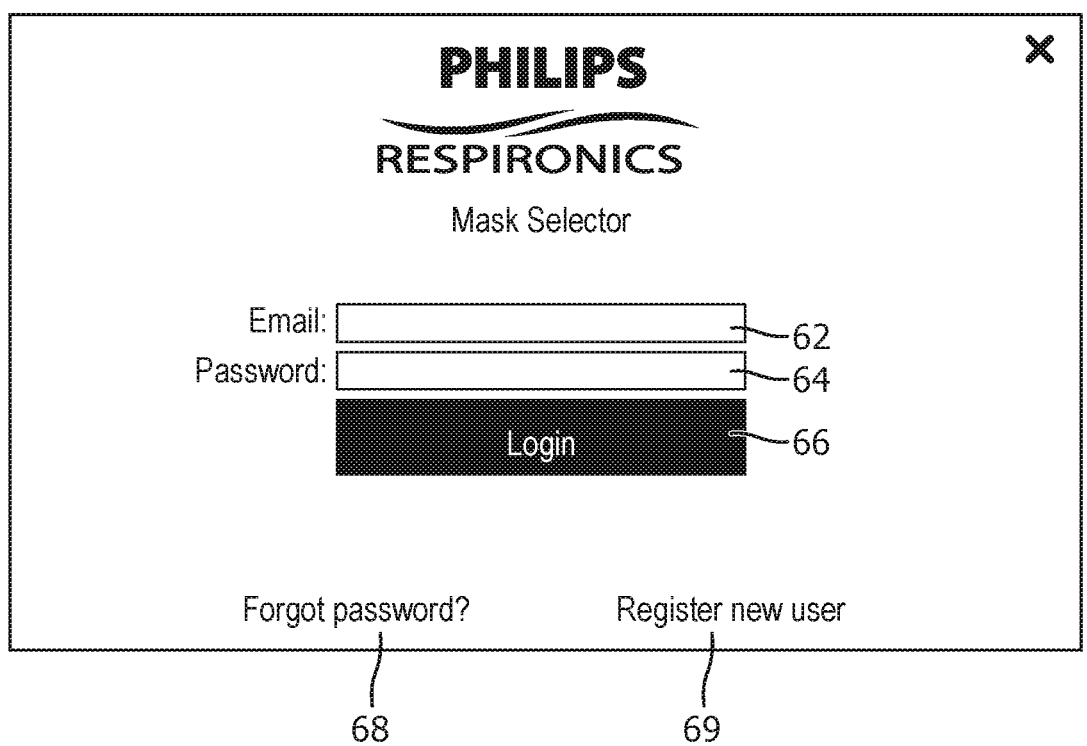

FIG. 6 is a schematic representation of a login screen 60 of software application/tool 41 that is displayed after splash screen 50. If a user has already established an account, the user can login to software application/tool 41 by entering his or her established account information, including email address and password, in boxes 62 and 64 and selecting login button 66. If, however, the user is a returning user who has forgotten his or her password, the user of software application/tool 41 may select the "Forgot Password" link 68. In response to selection of the "Forgot Password" link 68, software application/tool 41 will cause a request password reset code screen 70 shown in FIG. 7 to be displayed.

Figure 7:
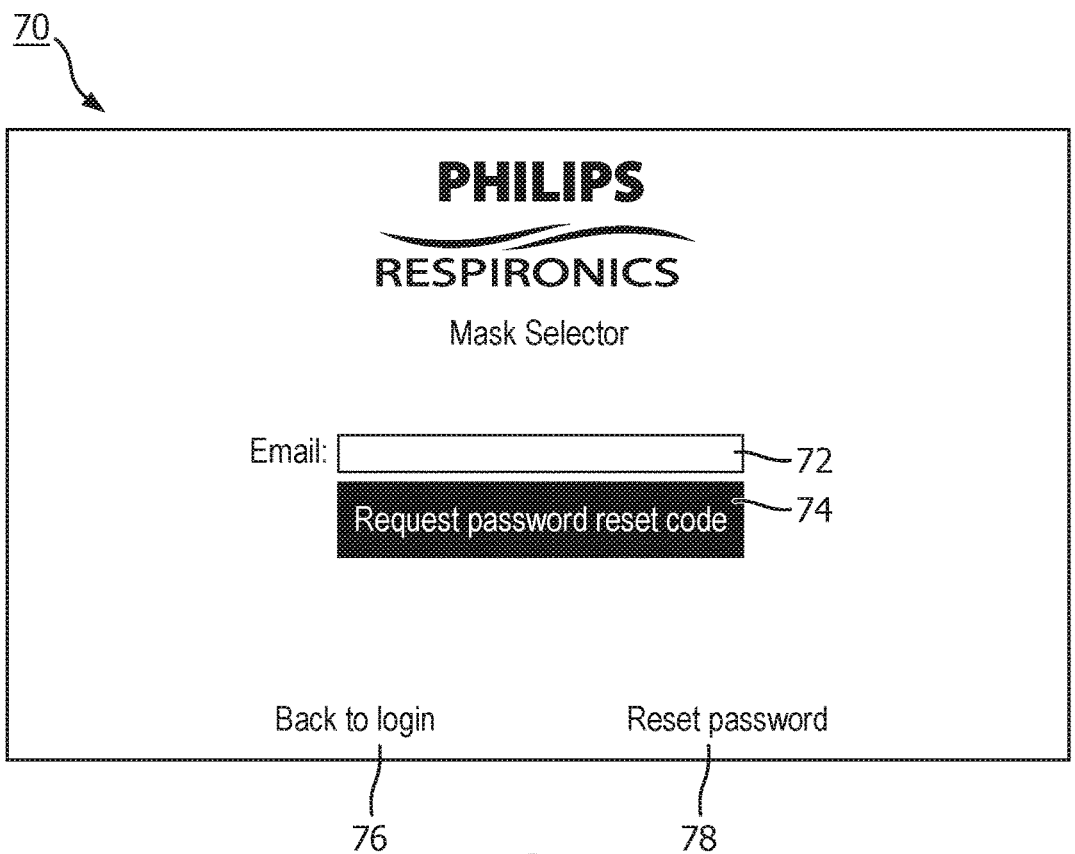
Figure 8:
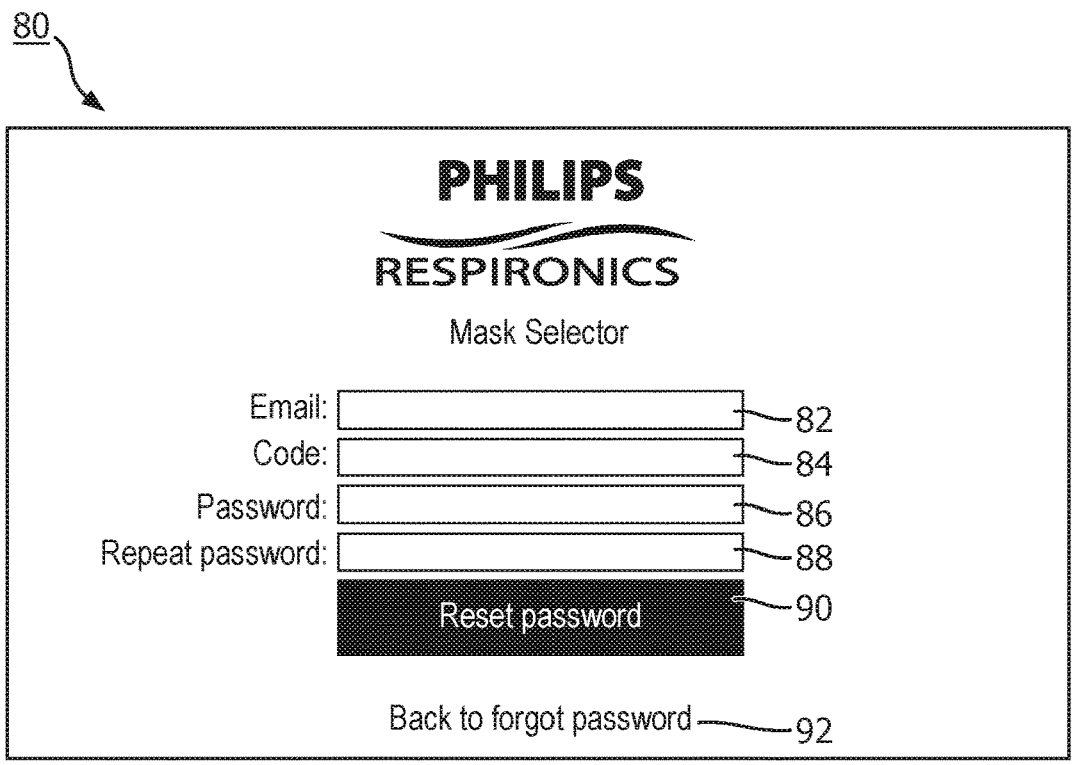

Referring now to the request password reset code screen 70 of FIG. 7, the user can request a password reset code by entering his or her e-mail address in box 72 and selecting "Request password reset code" button 74. Alternatively, the user can select a "Back to Login" link 76 if they would like to return to login screen 60 or select a "Reset password" link 78 if they would like to advance to a reset password screen 80, such as shown in FIG. 8 and described immediately below.

Figure 9:
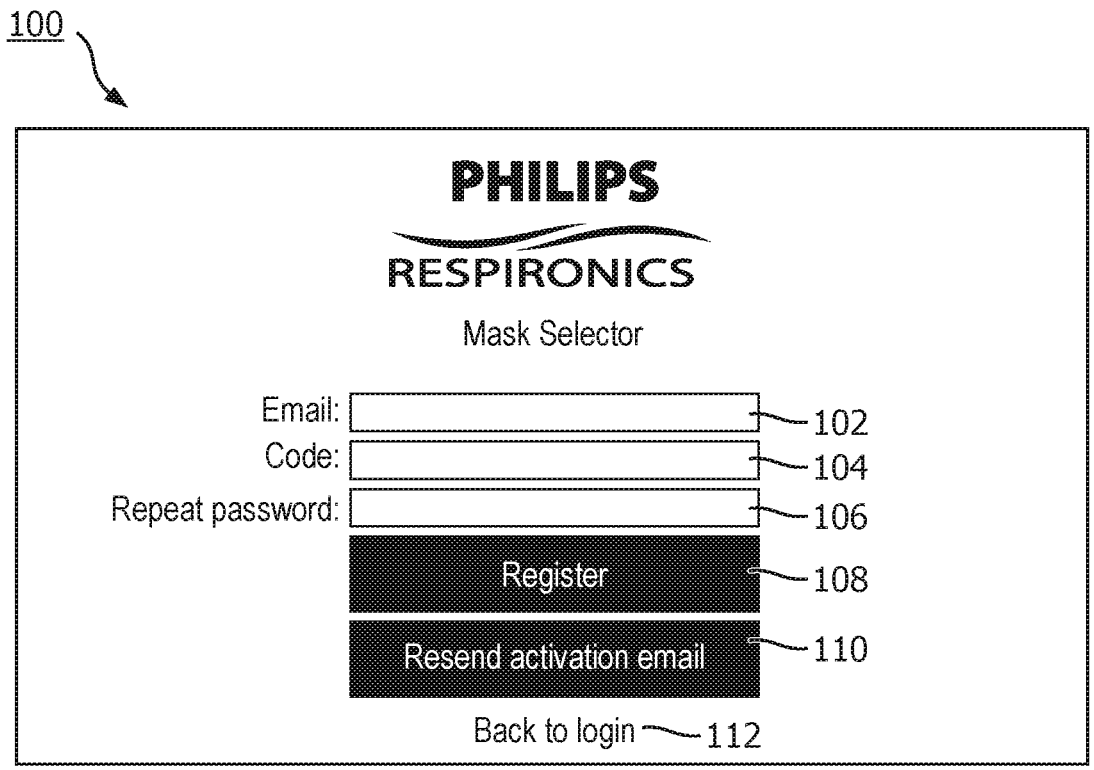

Upon selection of "Requesting password reset code" button 74, Logic Processing Component 18 will check whether the email address is in an associated database, and will send a multi-digit verification code to the aforementioned e-mail address only if it is determined that the email address is in the associated database. If this check fails, the user may be informed of the issue and may be redirected to a help portion of software application/tool 41, a help website, and/or to a register new user screen 100, such as shown in FIG. 9 and described below. If the check is successful and the verification code is sent, software application/tool 41 then displays reset password screen 80, such as shown in FIG. 8, for receiving the user e-mail and the reset code provided in the aforementioned e-mail in boxes 82 and 84. In another example embodiment, the user e-mail is automatically populated in box 82 from the entry of such address previously in box 72 of request password reset code screen 70. In addition to entering the code, the user is also required to enter and confirm a password to be used with his or her account in boxes 86 and 88. The updated password information is then submitted to the application software/tool 41 upon selection of a "Reset password" button 90 provide on reset password screen 80. If for some reason a user would like software application/tool 41 to return to the previous request password reset code screen 70, the user may select "Back to Forget Password" link 92 provided on reset password screen 80.

If the user is not a returning user but instead is a new user of software application/tool 41 without an established account, the user may instead select the "Register New User" link 69 in login screen 60. In response to selection of the "Register New User" link 69, software application/tool 41 will cause register new user screen 100 such as shown in FIG. 9 to be displayed. In order to create a new account, the user must enter certain information into register new user screen 100. In particular, the user must enter his or her email address into box 102. In the exemplary embodiment, the email address that is entered must be unique to system 8 and is used as the user's "username." The user is also required to enter and confirm a password to be used with his or her account in boxes 104 and 106 shown in FIG. 9. Thus, when a user attempts to create an account by entering their email address as just described and selecting "Register" button 108, Logic Processing Component 18 will check whether the email address is unique, and will authorize the creation of the account only if it is determined that the email address is unique. In such instance, an activation e-mail is then sent to the e-mail address provided by the user. Once the activation e-mail is received, the user clicks a link provided in the e-mail to confirm to Logic Processing Component 18 that he/she is an active user. If this check fails, the user may be informed of the issue and may be redirected to a help portion of software application/tool 41 or to a help website. If the check does not fail, but an activation e-mail is not received, the user may select "Resend Activation Email" button 110, prompting software application/tool 41 to resend an activation e-mail. A "Back to Login" link 112 is provided on register new user screen 100 which allows for the user to return to login screen 60 upon selection thereof.

Figure 10:
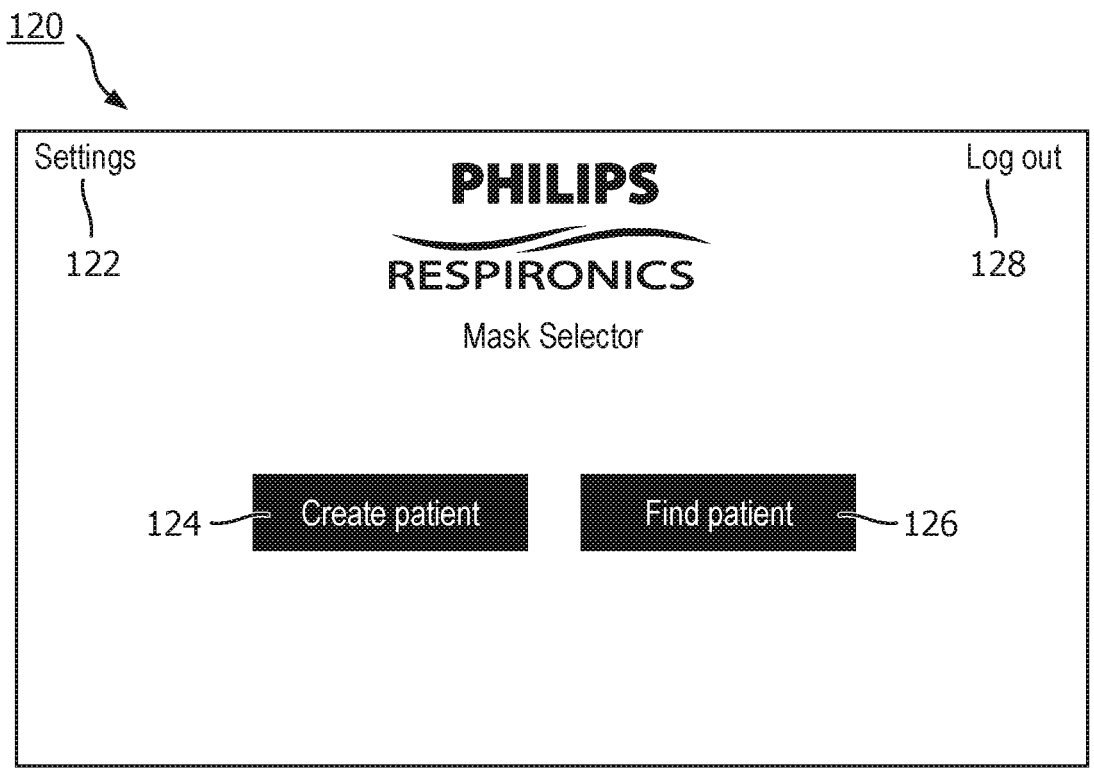

Once a user has successfully logged in via any of the ways previously described, software application/tool 41 will cause a home page 120 such as shown in FIG. 10 to be displayed where the user is presented with a number of options of how they may proceed. For example, a user may select among a "Settings" link 122, a "Create Patient" link 124, and a "Find Patient" link 126. A "Log Out" link 128 may also be selected, which will result in application/tool 41 logging the user out. Upon the user logging out, software application/tool 41 may return to login screen 60 or alternatively may terminate.

Figure 11:
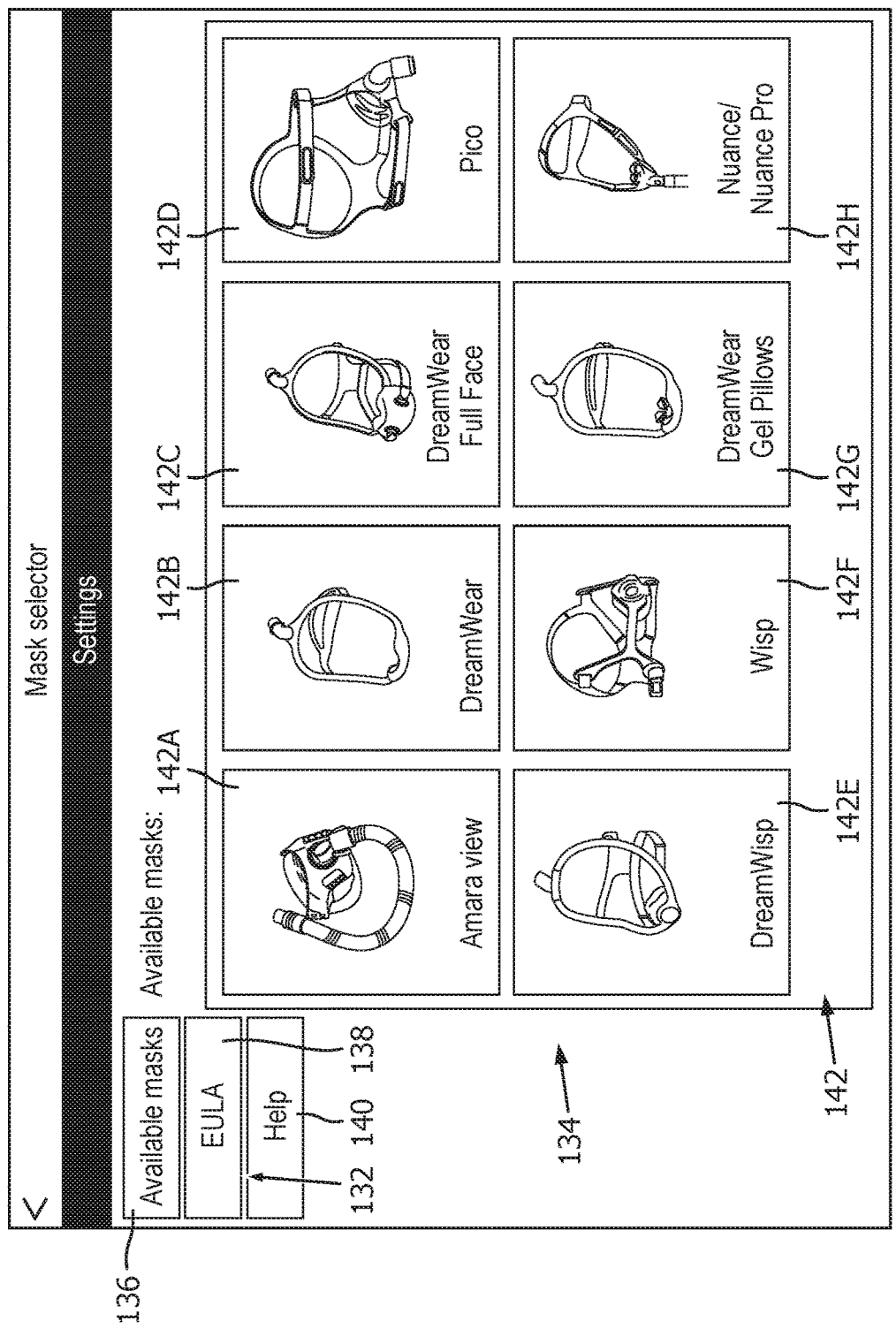
Figure 12:
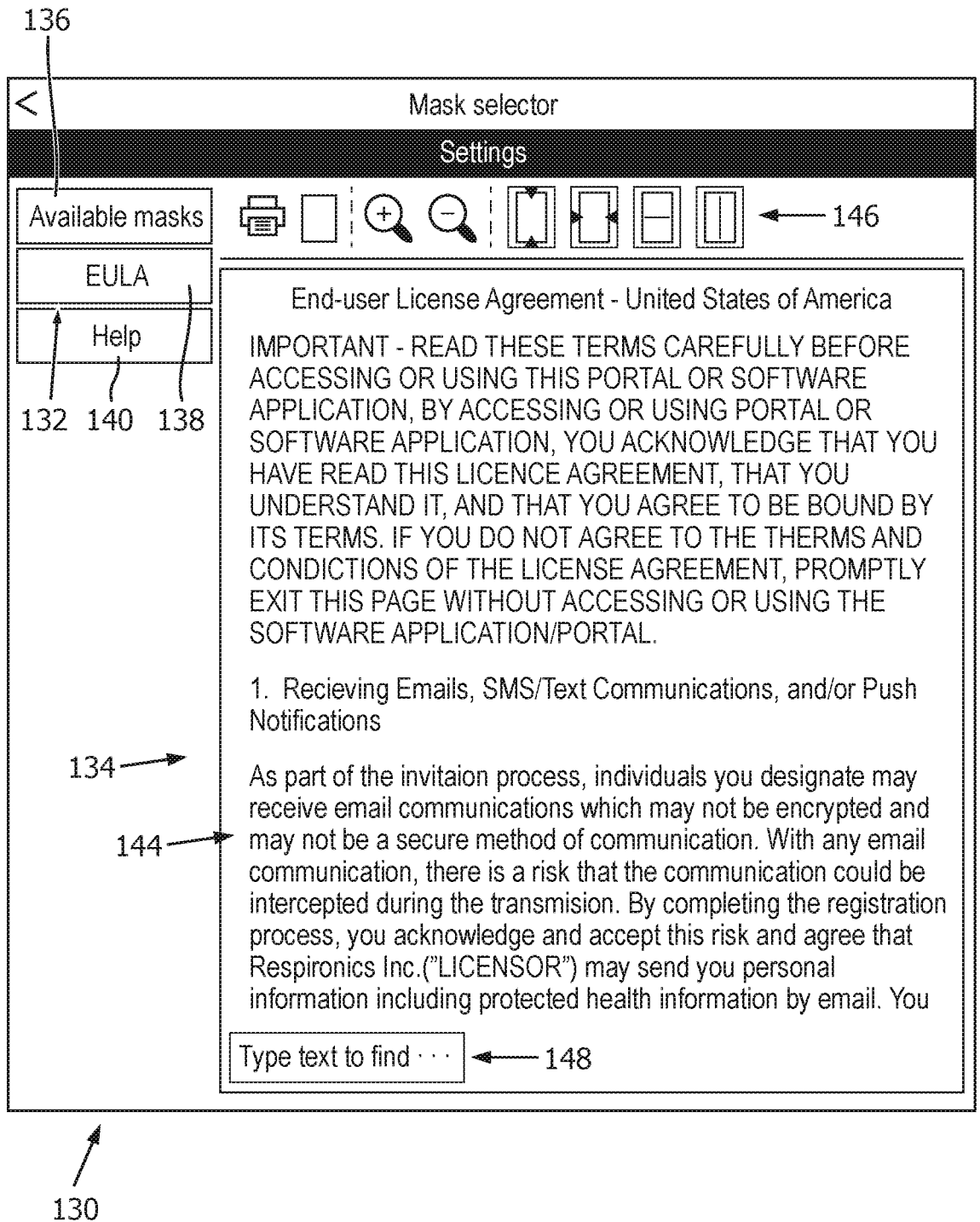
Figure 13:
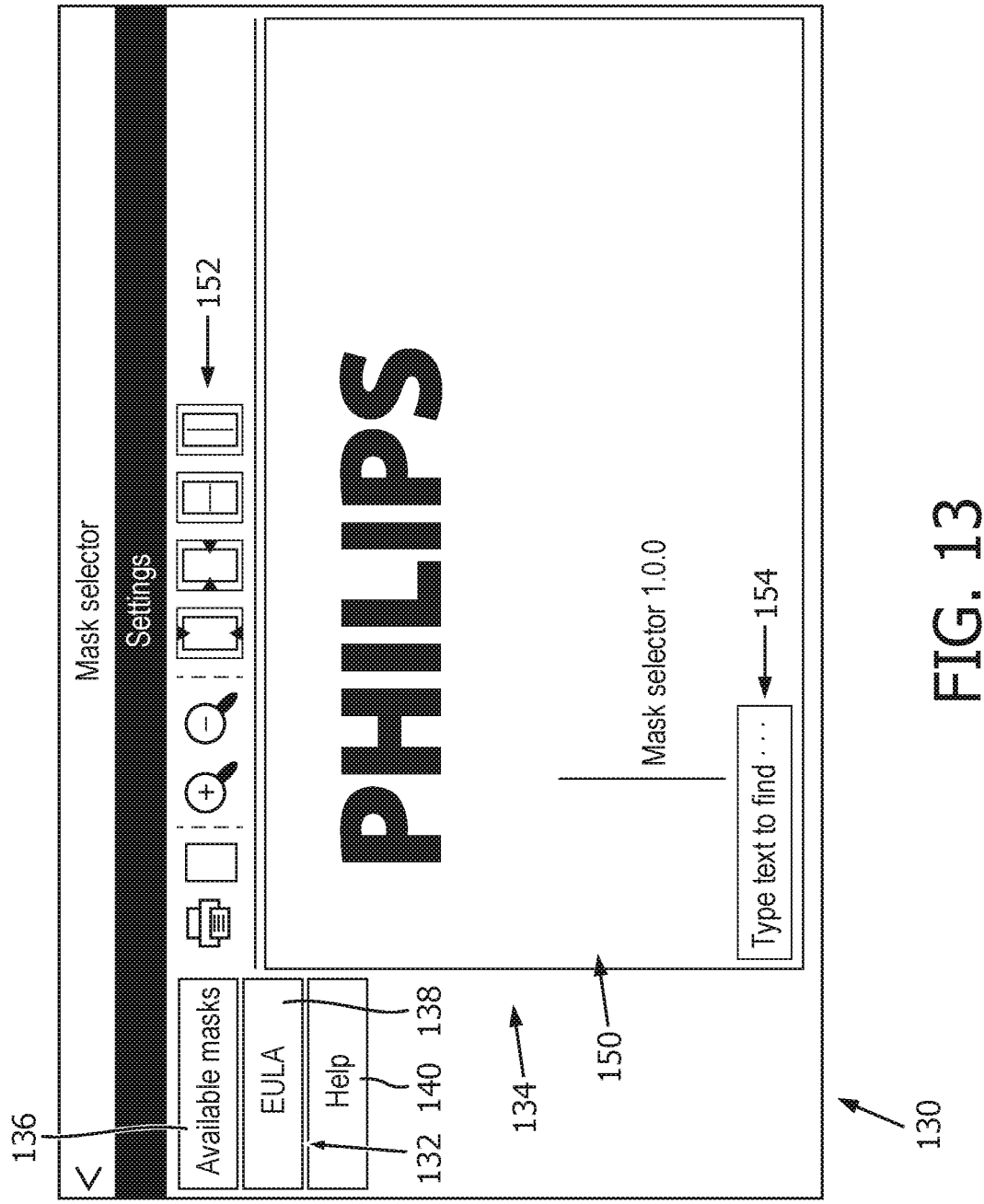

In response to selection of "Settings" link 122 on home page 120, software application/tool 41 will cause a settings page 130 such as shown in FIGS. 11-13 to be displayed. Settings screen 130 includes a menu 132 containing a listing selectable buttons, with each button listing a topic which can be displayed in a sub-display 134 of settings screen 132 when selected. In the example embodiment shown in FIGS. 11-13, menu 132 contains three selectable buttons: i.) "Available Masks" button 136, ii.) "EULA" button 138, and iii.) "Help" button 140. In response to "Available Masks" button 136 of settings page 130 being selected, such as shown in FIG. 11, software application/tool 41 will cause a listing 142 of mask families (e.g., 142A-142H) to be displayed in sub-display 134 which are available for consideration for a patient by software application/tool 41 as discussed in detail below. The user may then select or deselect mask families from the list (e.g., via highlighting, lowlighting, or any other suitable means) to include or preclude particular mask families from listing 142. This functionality allows for the mask provider (e.g., without limitation, a sleep lab, DME, etc.) to filter on only the masks that they currently have in inventory or can readily access and to remove masks from the process that they do not have in inventory or do not have ready access to.

In one example embodiment of the present invention the location from which the facial scan originates (e.g., one or more of the address, zip code, city, state, country, or any other suitable location or regional identifier) can be used to limit the selection of potential masks available for matching with the patient. Typically different geographical regions have different mask availability and popularity (e.g. North American DreamWear masks are available in different sizes than Japanese DreamWear masks; pillows masks are very popular in North America, but not popular in Japan). Mask recommendations can be adjusted to account for mask availability in a given geographic region or area within a region. Mask recommendations can also be adjusted based on other aspects of a given geographic region, e.g., nasal masks are preferred over full face masks in XX region; masks with snug fit are preferred over loose fit in XX region; custom masks are preferred over standard masks in XX region; low cost masks are preferred over more expensive masks in XX region; marketing is promoting YY mask in XX region; etc.

Selected masks for inclusion may be displayed in a first color (e.g., blue) while masks de-selected, or selected for not including may be displayed in a second color (e.g., white). As shown in the example of FIG. 11, listing 142 may include representative photos or other images of masks along with a name of such masks, however, it is to be appreciated that other formats may be utilized without varying from the scope of the present invention. In response to "EULA" button 138 being selected, such as shown in FIG. 12, software application/tool 41 will cause an end user license agreement (EULA) 144 governing the usage of software application/tool 41 to be displayed in sub-display 134. Selectable tools 146 (e.g., forward, copy, zoom in/out, expand, etc.) may be provided to assist the user in viewing EULA 134. A search tool 148 may also be provided to assist the user in navigating EULA 134. In response to "Help" button 138 being selected, such as shown in FIG. 13, software application/tool 41 will cause a help document 150 containing instructions related to the use of software application/tool 41 to be displayed in sub-display 134. Selectable tools 152 (e.g., forward, copy, zoom in/out, expand, etc.) may be provided to assist the user in viewing help document 150. A search tool 154 may also be provided to assist the user in navigating help document 150.

In response to selection of "Create Patient" link 124 on home page 120, software application/tool 41 will cause a create patient page 160 such as shown in FIG. 14 to be displayed. The user may then enter information for a new patient such as the scan date, date of birth, first and last name, as well as a patient ID (e.g., any combination of letters and/or numerals) in boxes 162, 164, 166, 168, 170. Further, the user may provide an indication, e.g., by selecting "Yes" button 171, that the patient is a compliant patient presently using a mask, and thus is potentially looking for a better mask. The purpose of which is discussed further below. Responsive to the user selecting a "Next" button 172 provided on create patient page 160, software application/tool 41 will cause a scanning instructions page 180 to be displayed.

Figure 15:
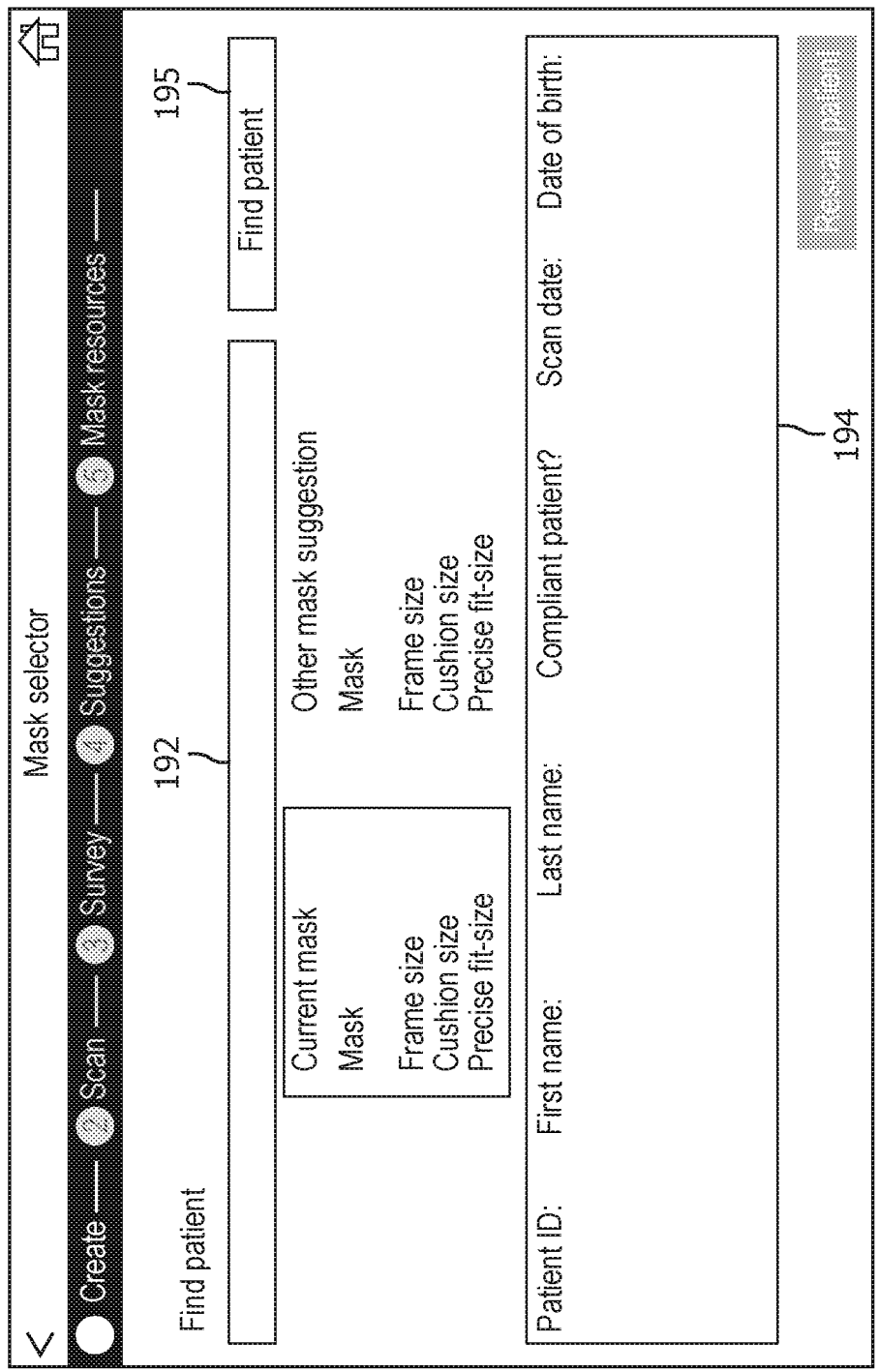
Figure 16:
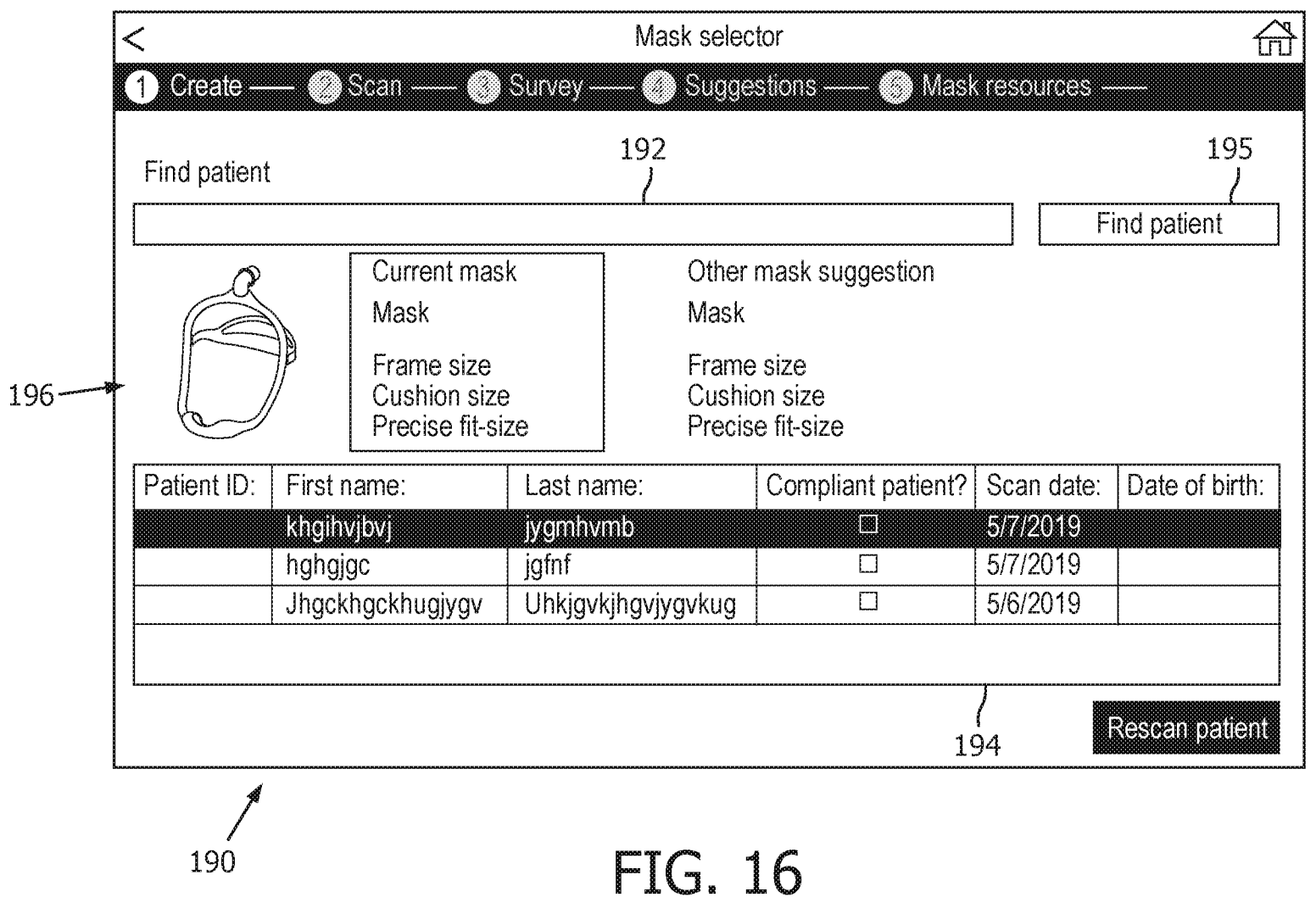

In response to selection of "Find Patient" link 126 on home page 120, software application/tool 41 will cause a find patient page 190 such as shown in FIG. 15 to be displayed. The user may then enter information pertaining to an existing patient (e.g., date of birth, first name, last name, patient ID) in a box 192 provided on find patient page 190. The user can then cause software application/tool 41 to display a listing of search results in a search results area 194 that are related to the information entered in box 192 by selecting a find patient button 195. In one example embodiment, the results displayed in search results area 194 are editable. In response to selection of particular results in area 194 corresponding to a particular patient provided in box 192, software application/tool 41 will cause further results 196 in regard to the particular patient (e.g., a current mask being used by a patient and/or previous masks suggested for use by the patient) to be displayed on find patient page 190, such as shown in FIG. 16. Such further results 196 may be employed by a user to suggest/provide a new mask to the particular patient. If the user desires to acquire a new scan of the patient, the user may select a "Rescan Patient" button 198 provided on find patient page 190. In response to selection of "Rescan Patient" button 198, software application/tool 41 will cause the scanning instructions page 180 of FIG. 13 to be displayed.

Figure 17:
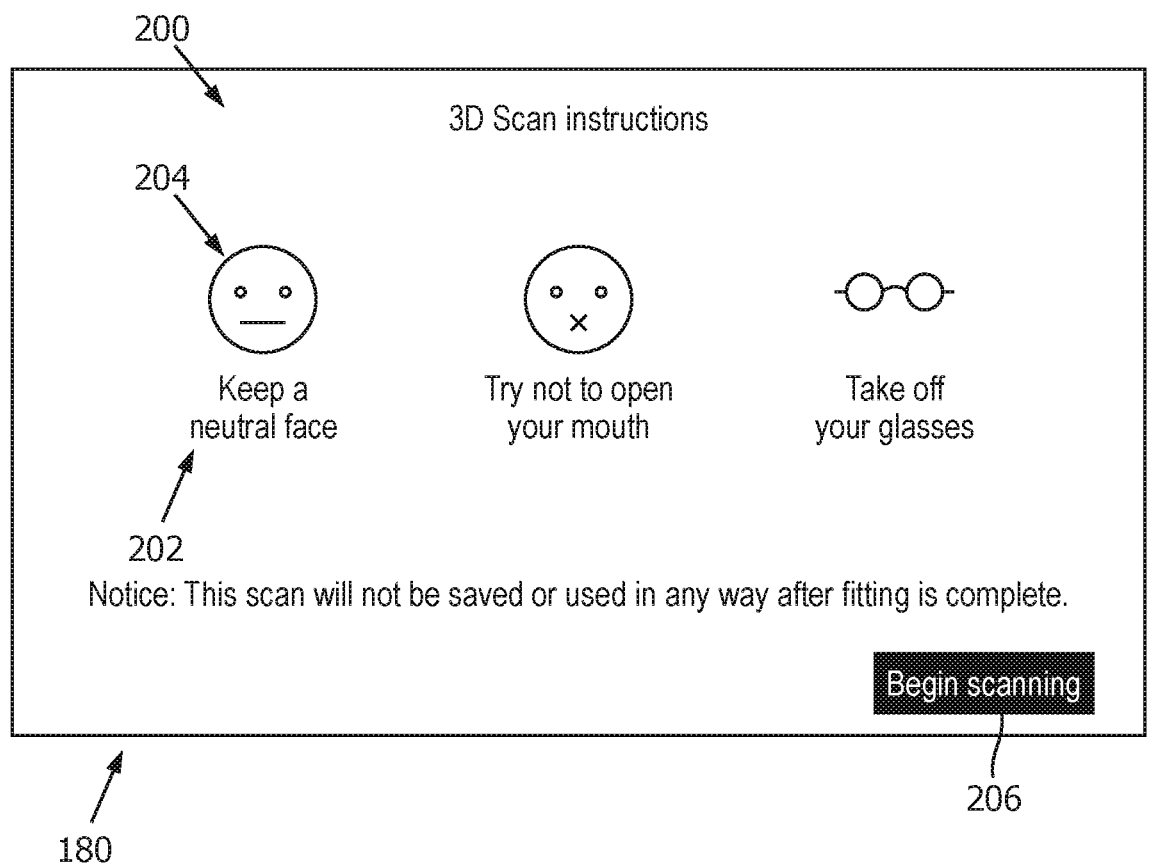

Referring now to FIG. 17, scanning instructions page 180 includes some general instructions 200 that should be followed in order to obtain an optimum 3D scan of a patient's face. Instructions 200 may include text instructions 202 and/or visual instructions 204. The user may proceed from scanning instructions page 180 by selecting a "Begin Scanning" button 206 provided on scanning instructions page 180.

Upon selection of "Begin Scanning" button 206, software application/tool 41 will cause a patient scanning screen 220 to be displayed, as will now be discussed in conjunction with FIGS. 18-29. In the example embodiment described herein, scanning of a patient P is carried out by a user such as previously described (e.g., without limitation, a clinician or DME provider) holding Visual Presentation and Interaction Component 20 using rearward facing camera 30 and 3D imaging apparatus 32 of Visual Presentation and Interaction Component 20 to capture images of patient P. However, it is to be appreciated that scanning of a patient may be carried out by the patient them self in a "selfie" type scanning mode using forward facing camera 28 and 3D imaging apparatus of Visual Presentation and Interaction Component 20. Additionally, it is to be appreciated that other image capturing devices in addition to, or in place of, one or more of forward facing camera 28, rearward facing camera 30, and/or 3D imaging apparatus 32 may be employed for capturing images of a patient without varying from the scope of the present invention.

Patient scanning screen 220 includes an image display area 222 and a message area 224. Image display area 222 may include an indicator 226, which in the example illustrated is in the form of a dashed elliptical line, provided therein for assisting in obtaining optimum placement of Visual Presentation and Interaction Component 20 with respect to patient P or vice-versa. In the example embodiment illustrated in FIGS. 18-29, video images captured by rearward facing camera 30 are displayed in image display area 222 to help guide the user in obtaining a successful 3D scan. Alternatively, video images captured by forward facing camera 28 may be displayed in image display area 222 if electronic device is being operated by the patient them self to conduct a 3D scan of his or herself. In such second instance, images captured by front facing camera 28 would be used to assist the patient in obtaining a successful 3D scan of his or herself.

Figure 18:
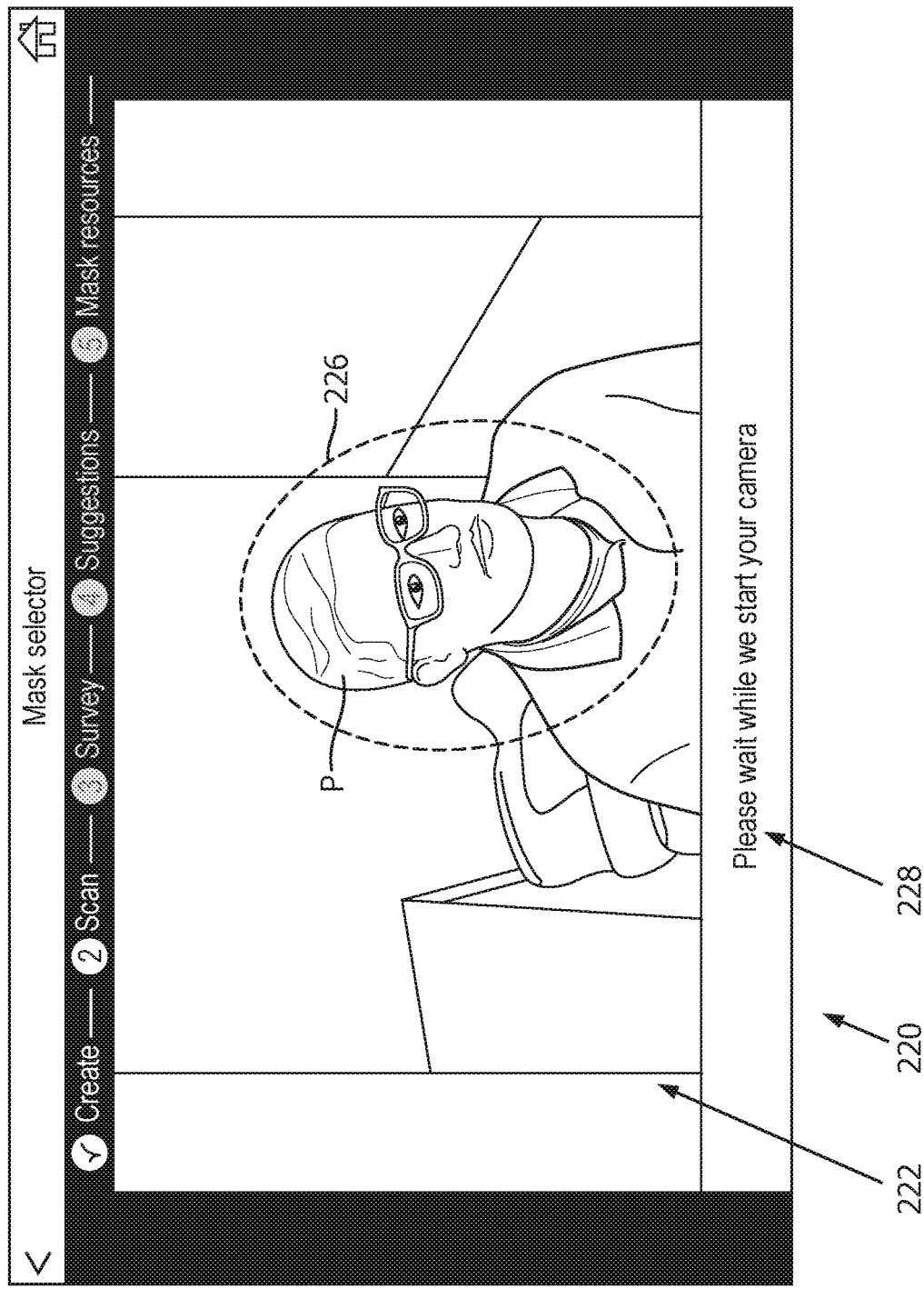
Figure 19:
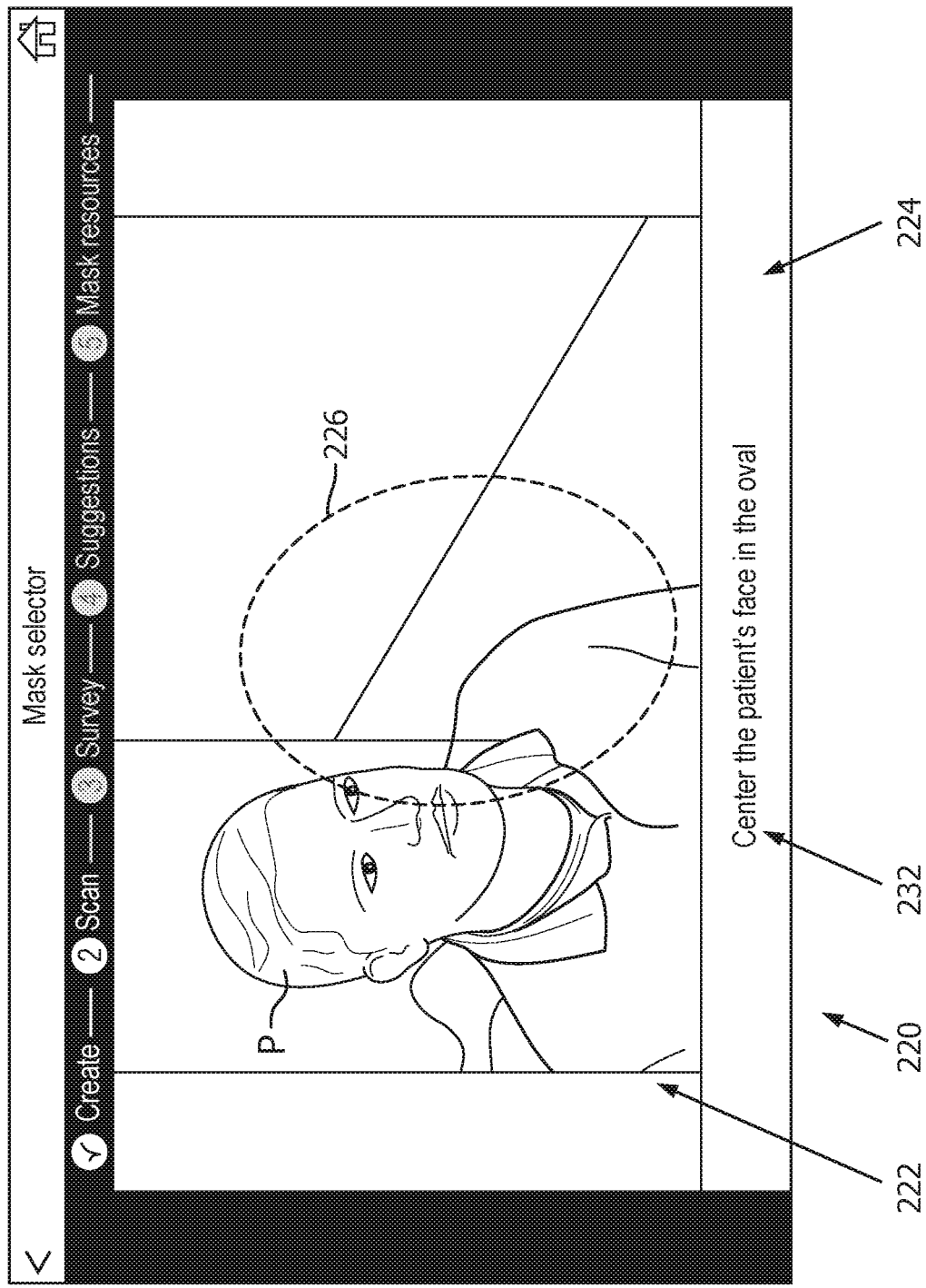
Figure 20:
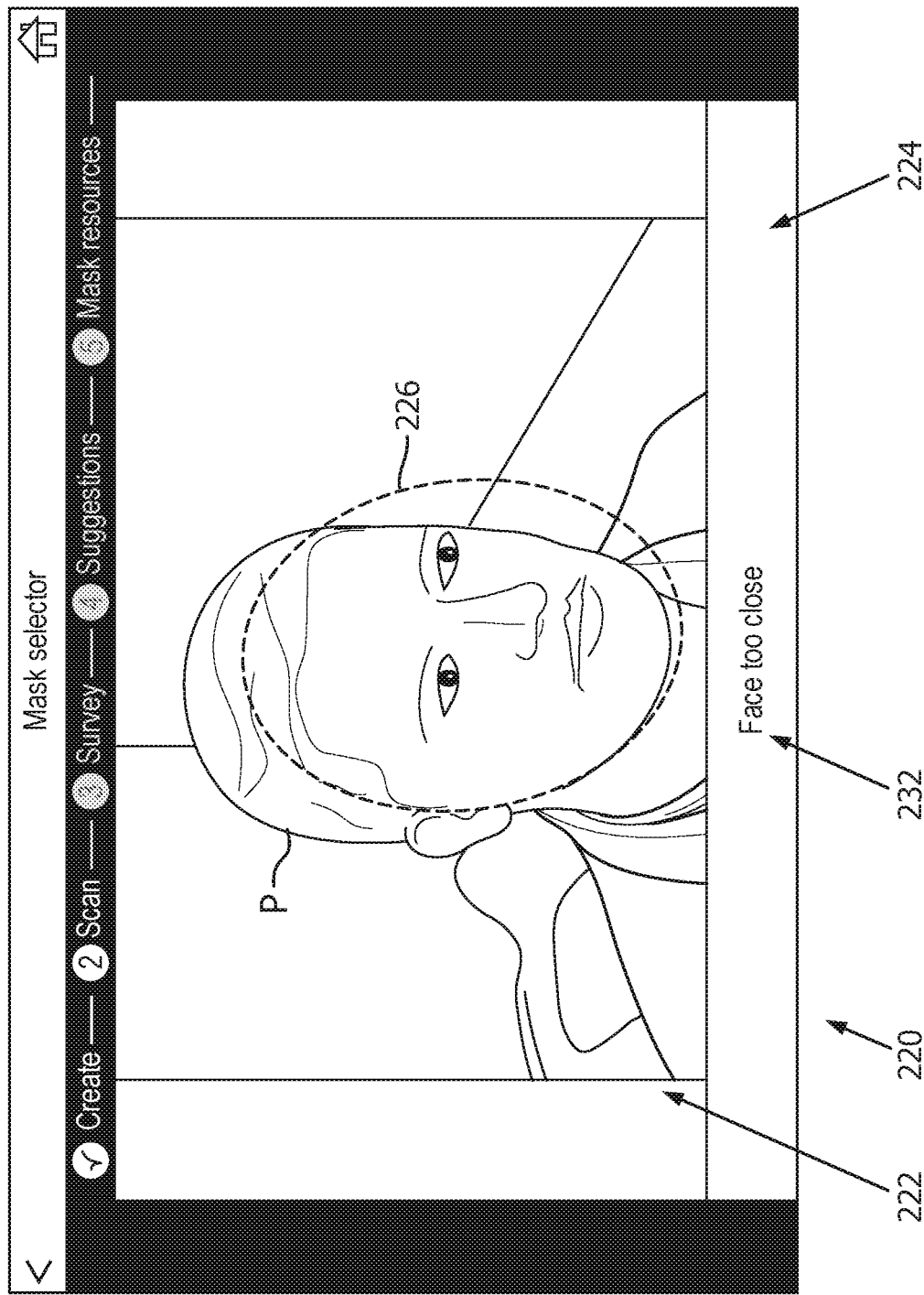
Figure 21:
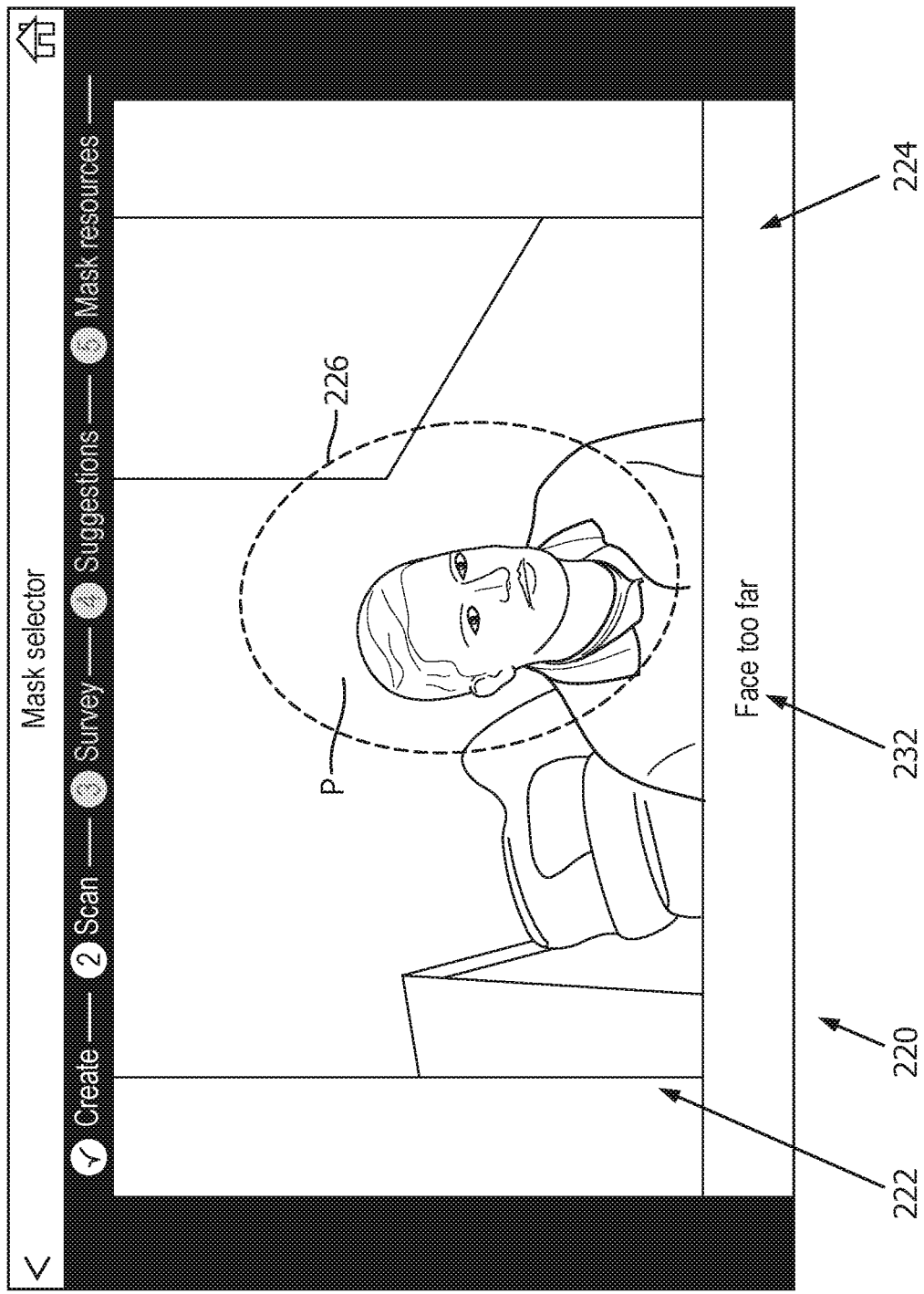
Figure 22:
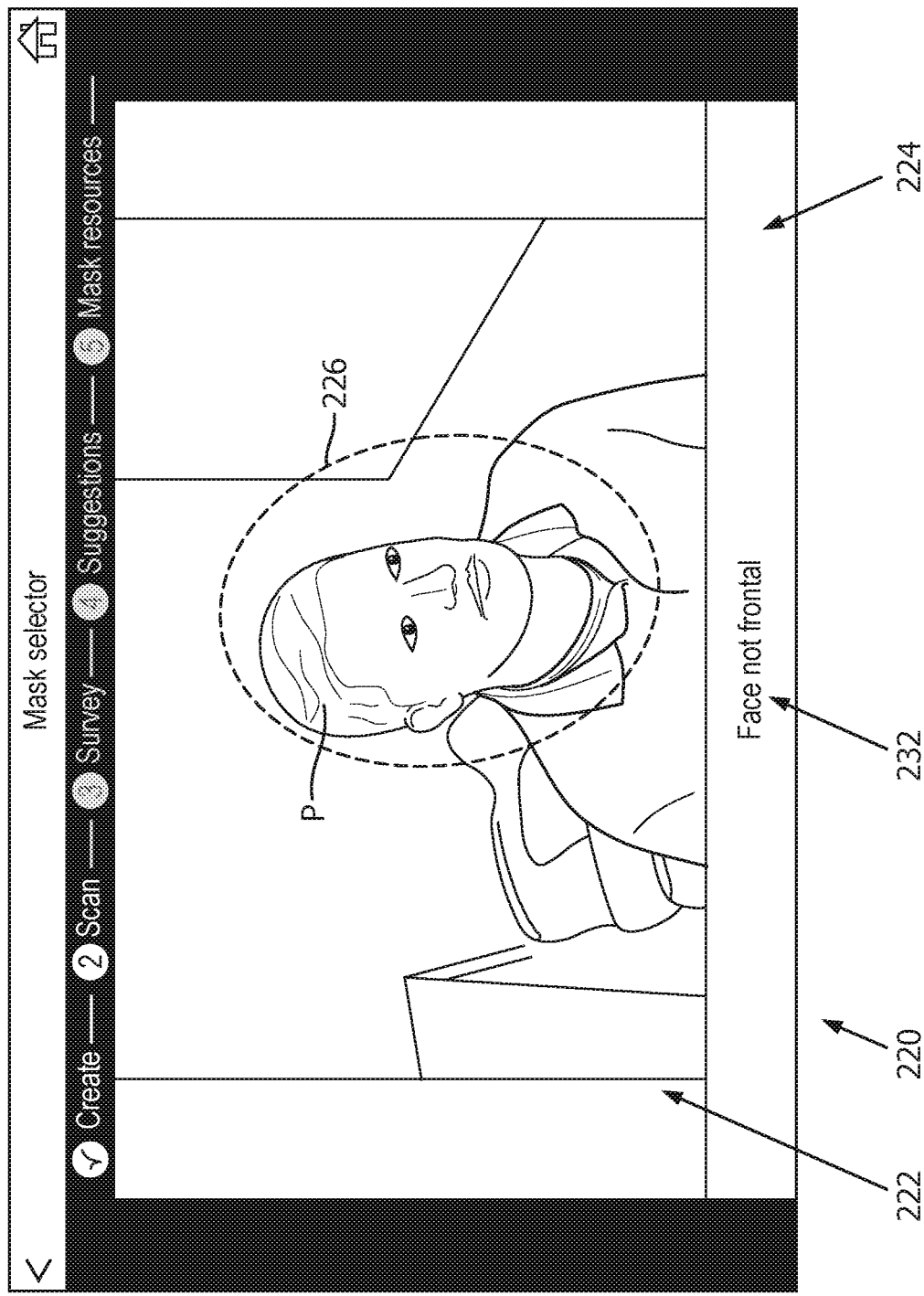
Figure 23:
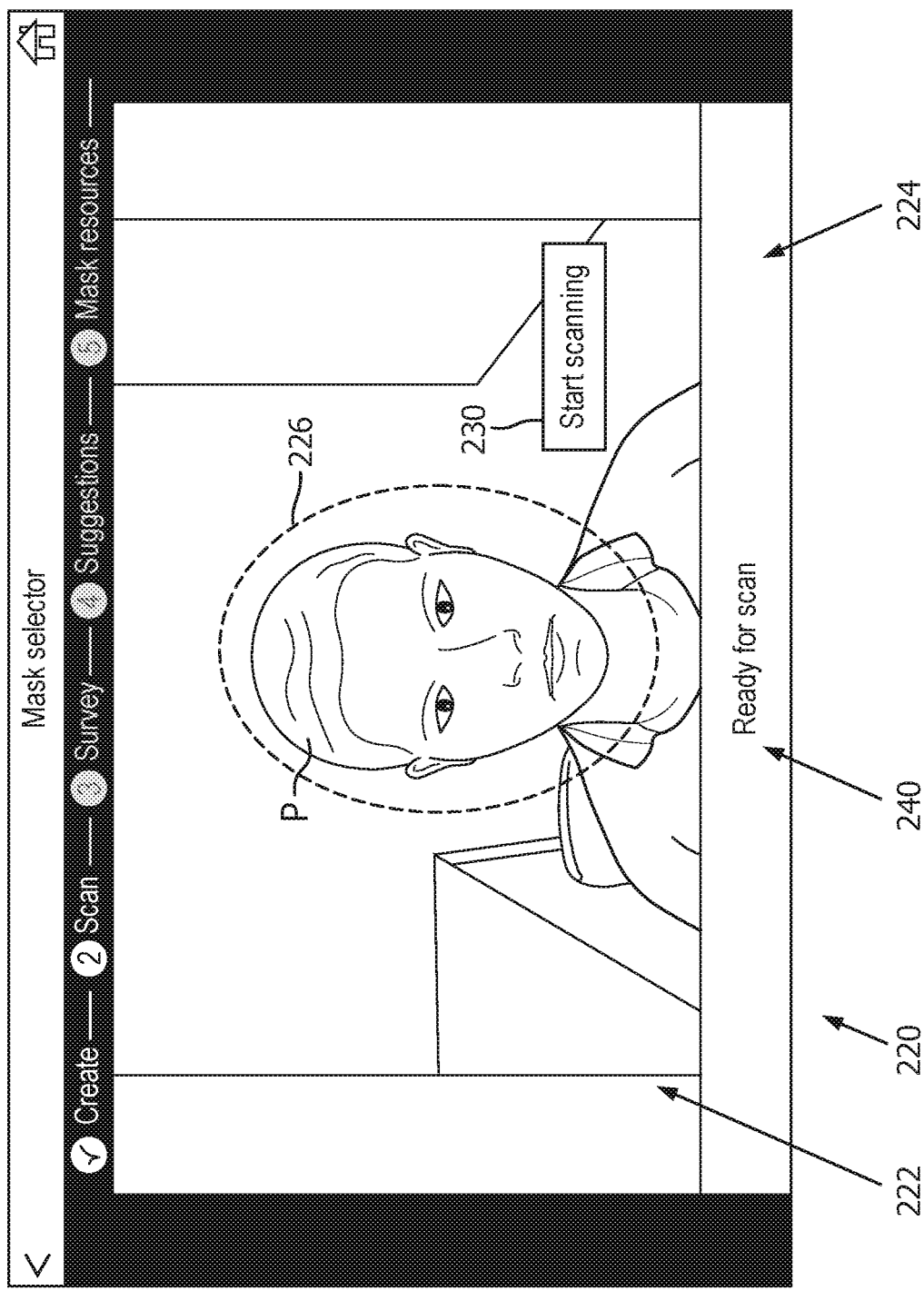
Figure 24:
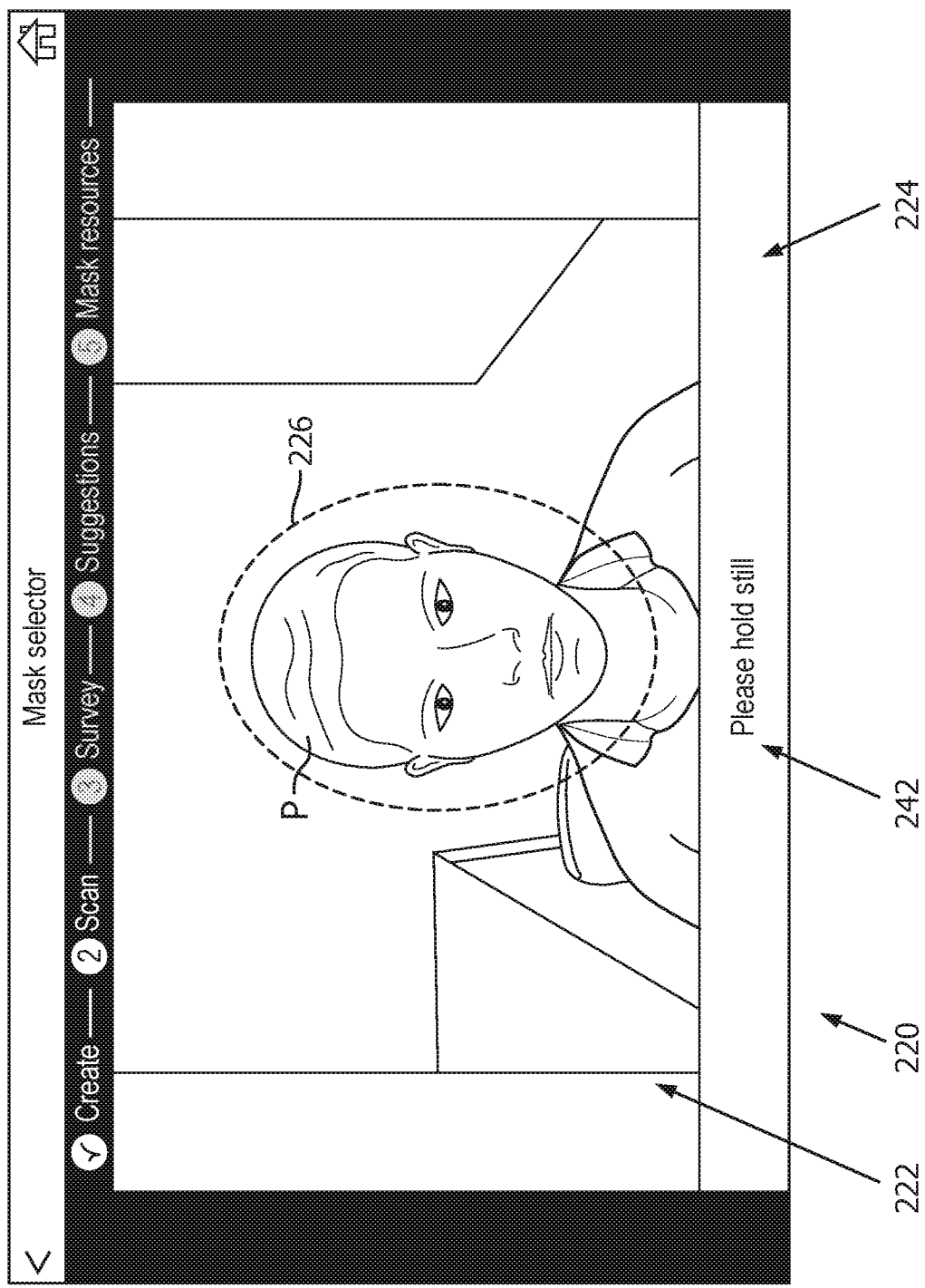
Figure 25:
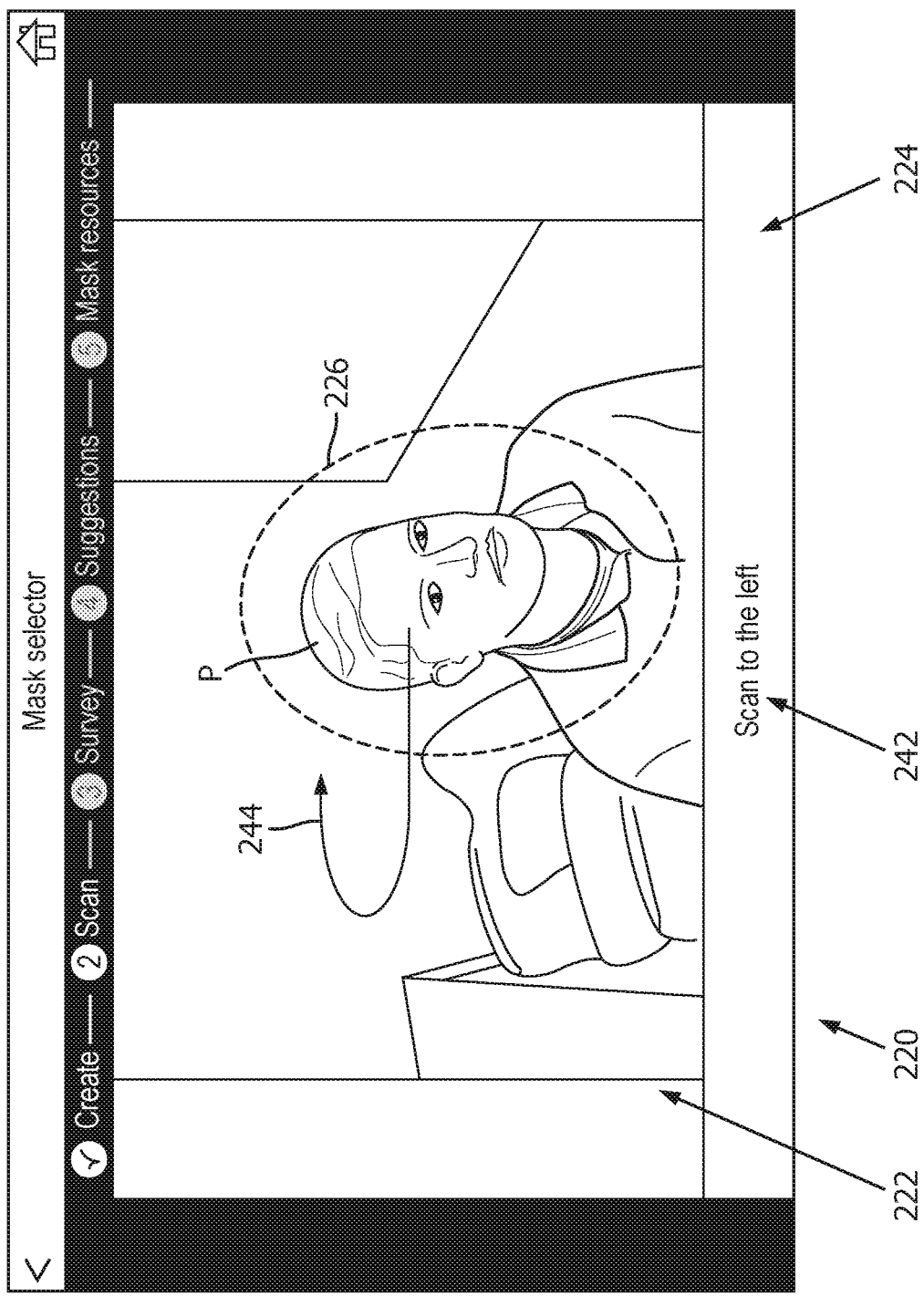
Figure 26:
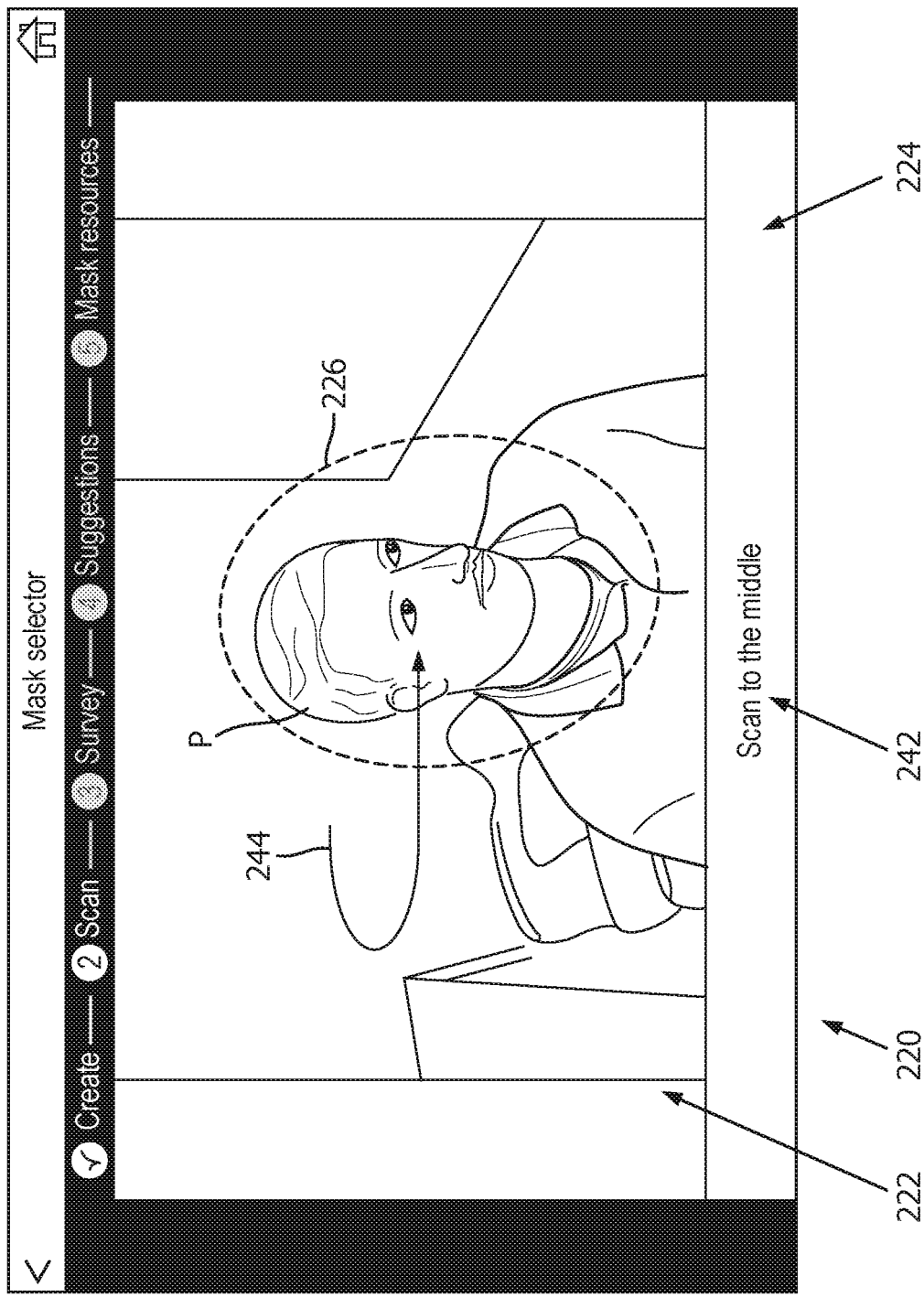
Figure 27:
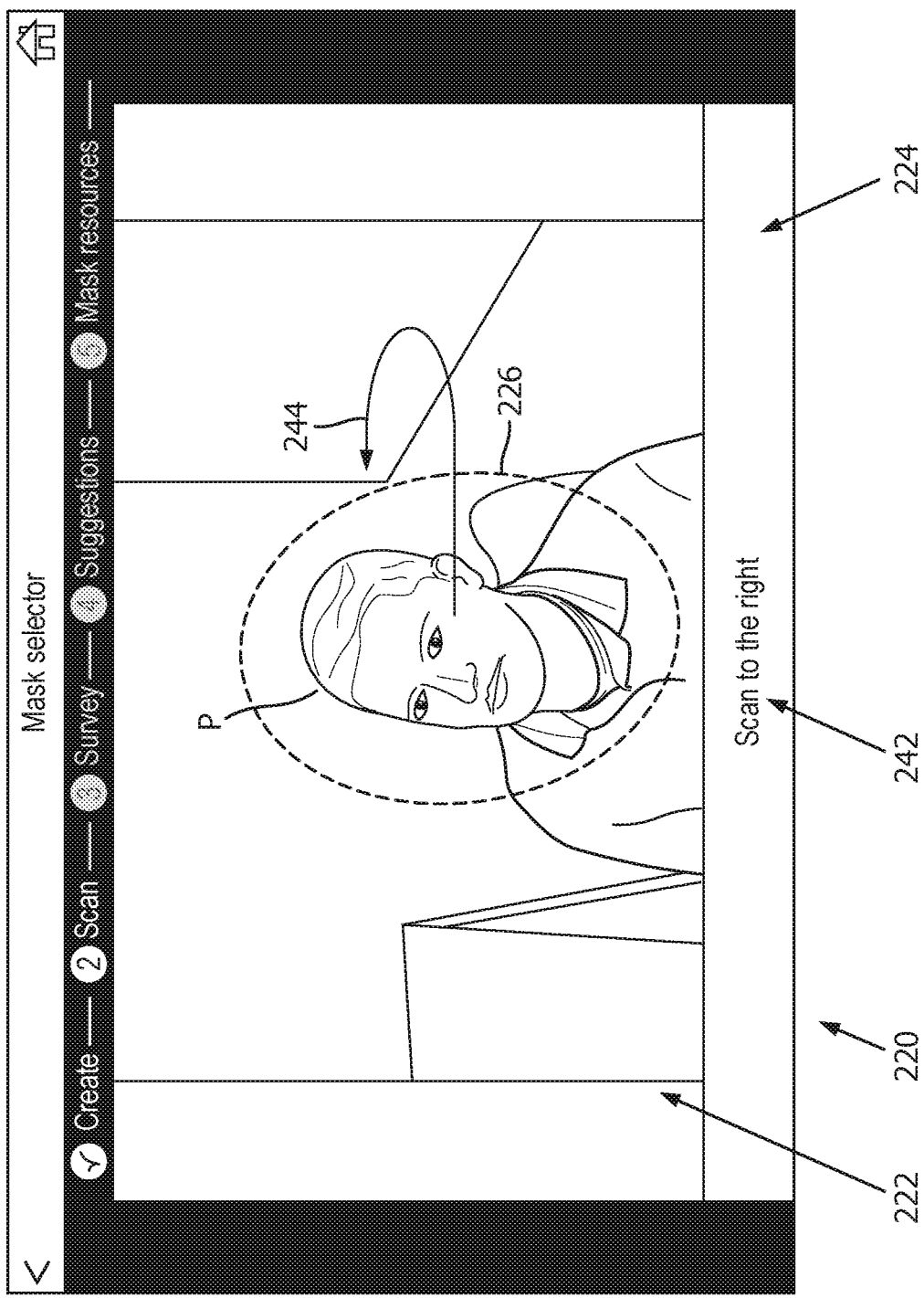
Figure 28:
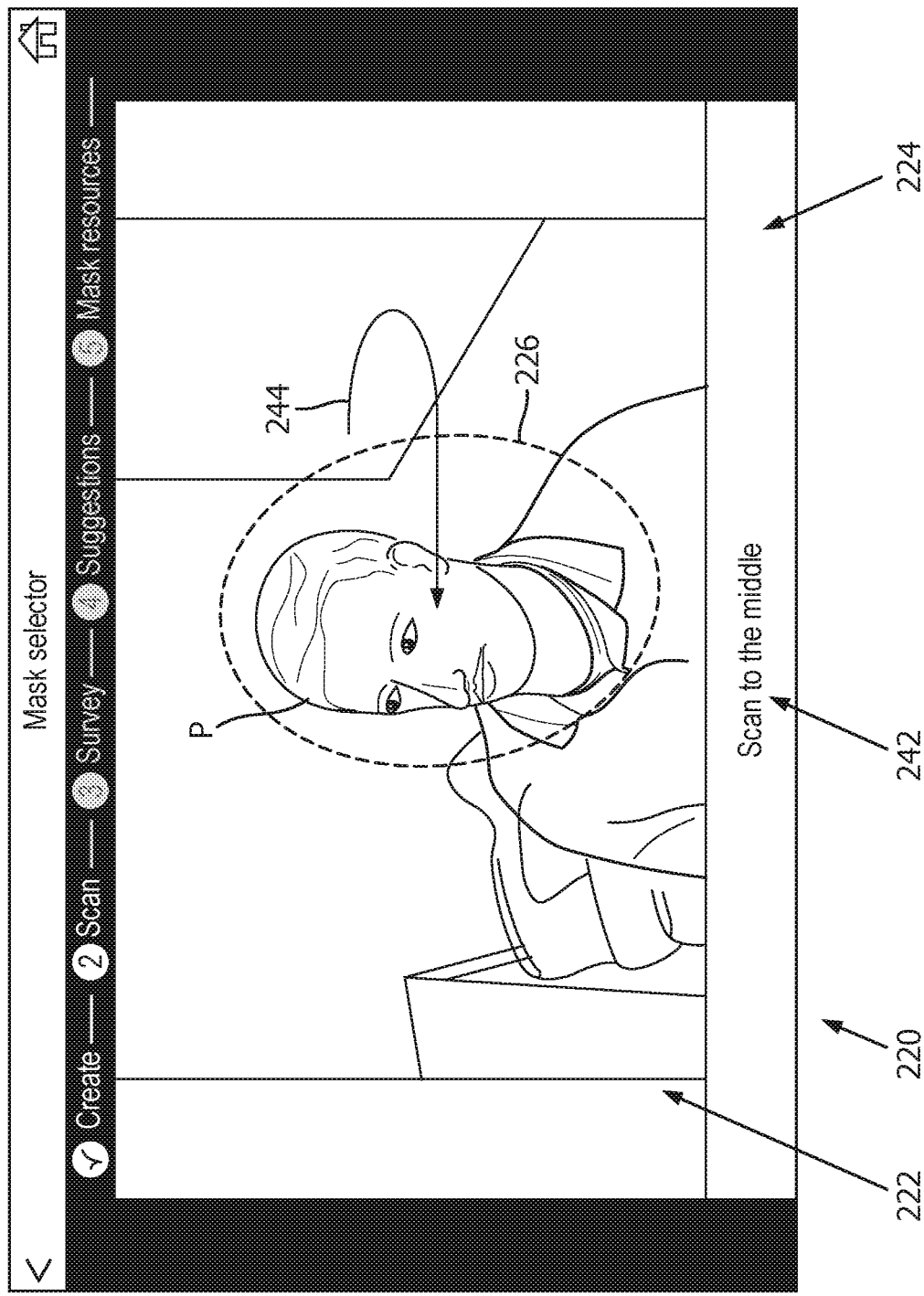

Referring now to FIG. 18, when patient scanning screen 220 is first displayed a wait message 228 may be provided in message area 224. Additionally, or alternatively, indicator 226 may be displayed in a first color, e.g., white, to indicate that scanning is not yet ready to begin. When software application/tool 41 is ready to commence scanning, software application/tool 41 provides a "Start Scanning" button 230 on scanning screen 220, such as shown in FIG. 23. However, as shown in FIGS. 18-22, if software application/tool 41 determines that the face of patient P is not located properly in the images captured by rearward facing camera 30 (or forward facing camera 28 depending on the embodiment), i.e., not positioned correctly with respect to indicator 226, "Start Scanning" button 230 may not be provided on scanning screen 220 or may be provided but in a ghosted form or otherwise indicated as being un-selectable. In such instances where software application/tool 41 has determined that the face of patient P is not properly located/positioned, a corrective instruction 232 is provided in message area 224 to assist in correcting the positioning of the patient. In addition to, or instead of such corrective instruction, indicator 226 may be displayed in a negative indicating color (e.g., red) to indicate that the position of patient P within the image is not acceptable. As shown in the examples of FIGS. 19-22, such corrective instruction 232 may include, for example, without limitation, an instruction to: center the face of patient P, move the face of patient P closer or further away, and direct the face be oriented more toward the camera(s).

As shown in FIG. 23, once software application/tool 41 determines that the face of patient P is properly positioned/oriented in the images captured by camera 28, a ready to scan message 240 is displayed in message area 224 and/or indicator 226 changes to a positive color (e.g., green), and "Start Scanning" button 230 is displayed and/or becomes selectable.

Upon selection of "Start Scanning" button 230, software application/tool 41 begins scanning of patient P. During scanning, software application/tool 41 provides instructions 242, such as, without limitation, "please hold still", "scan to the left", "scan to the middle", and "scan to the right", for moving Visual Presentation and Interaction Component 20 (when using rearward facing camera 30 as shown in the example in FIGS. 18-29) or the head of patient P (when in "selfie" mode using forward facing camera 28). Additionally, or instead of such instructions 242, one or more graphical indicators such as arrow 244 may be provided to assist in directing movement of one or both of the head of patient P or Visual Presentation and Interaction Component 20 during the scanning operation.

Figure 29:
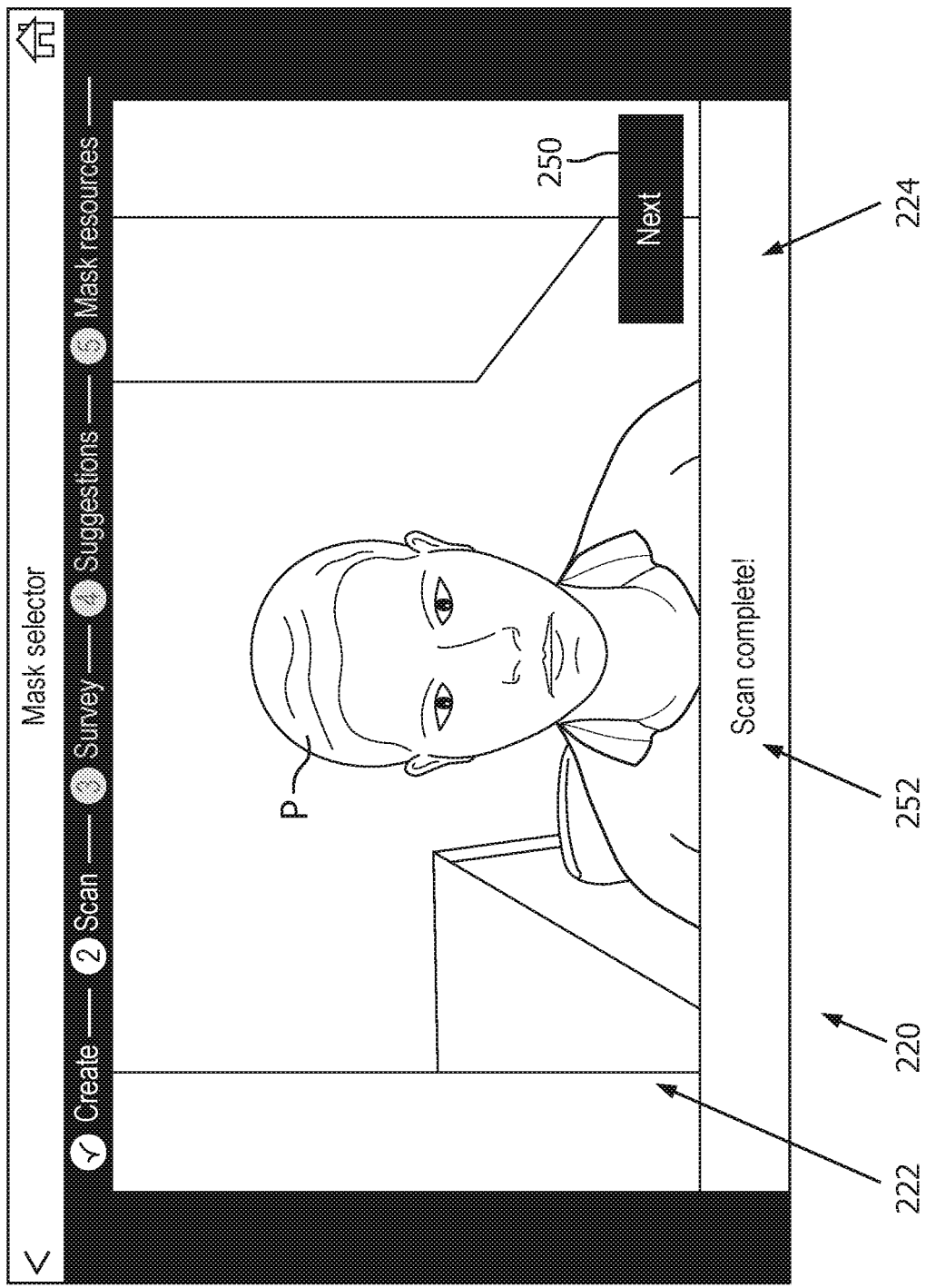

Referring now to FIG. 29, when software application/tool 41 determines that the scanning operation is complete, a "Next" button 250 is provided on patient scanning screen 220. Additionally, a "Scan complete" message 252 may be provided in message area 224 and/or indicator 226 may disappear or change to yet a further color.

Figure 30:
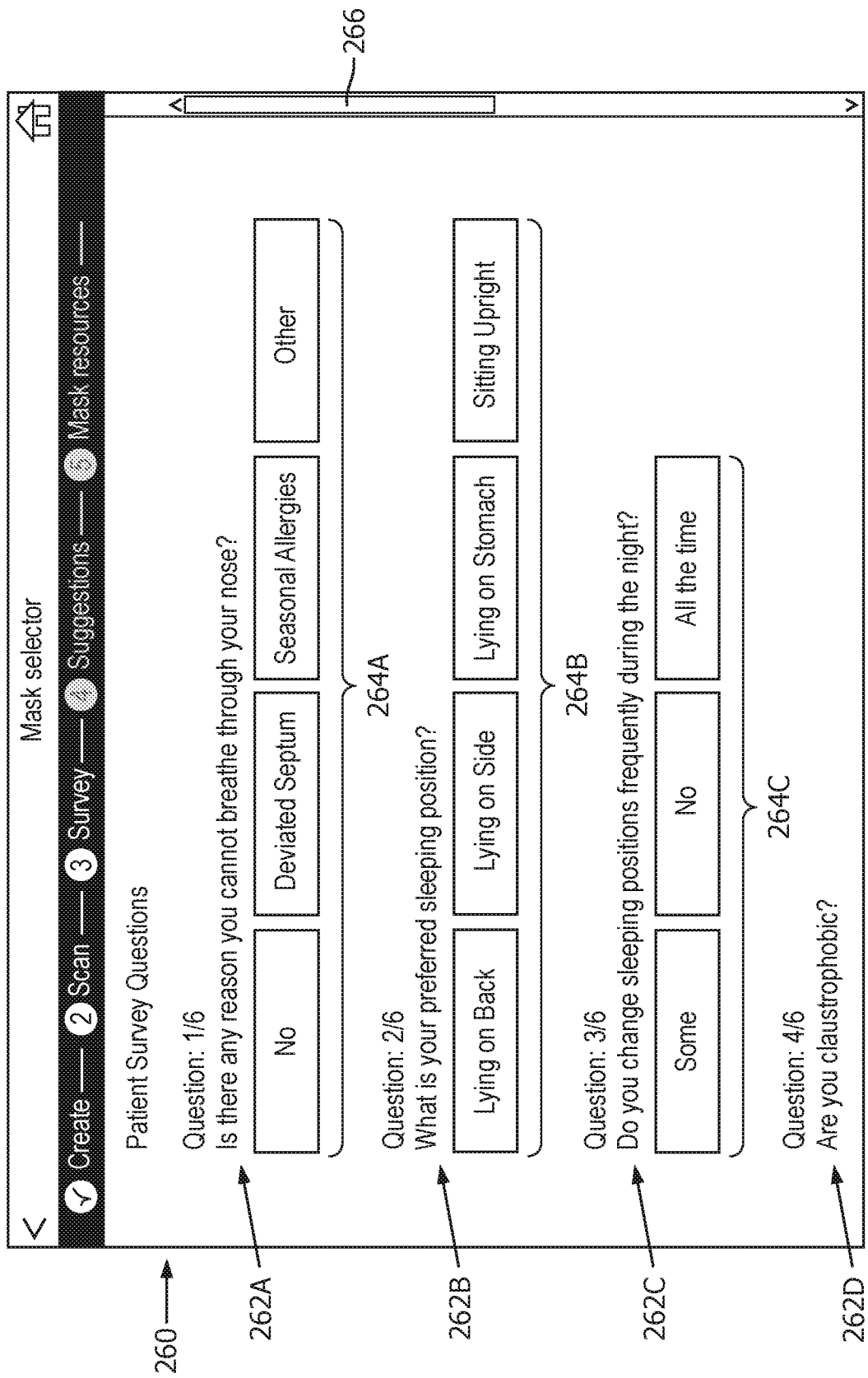
Figure 31:
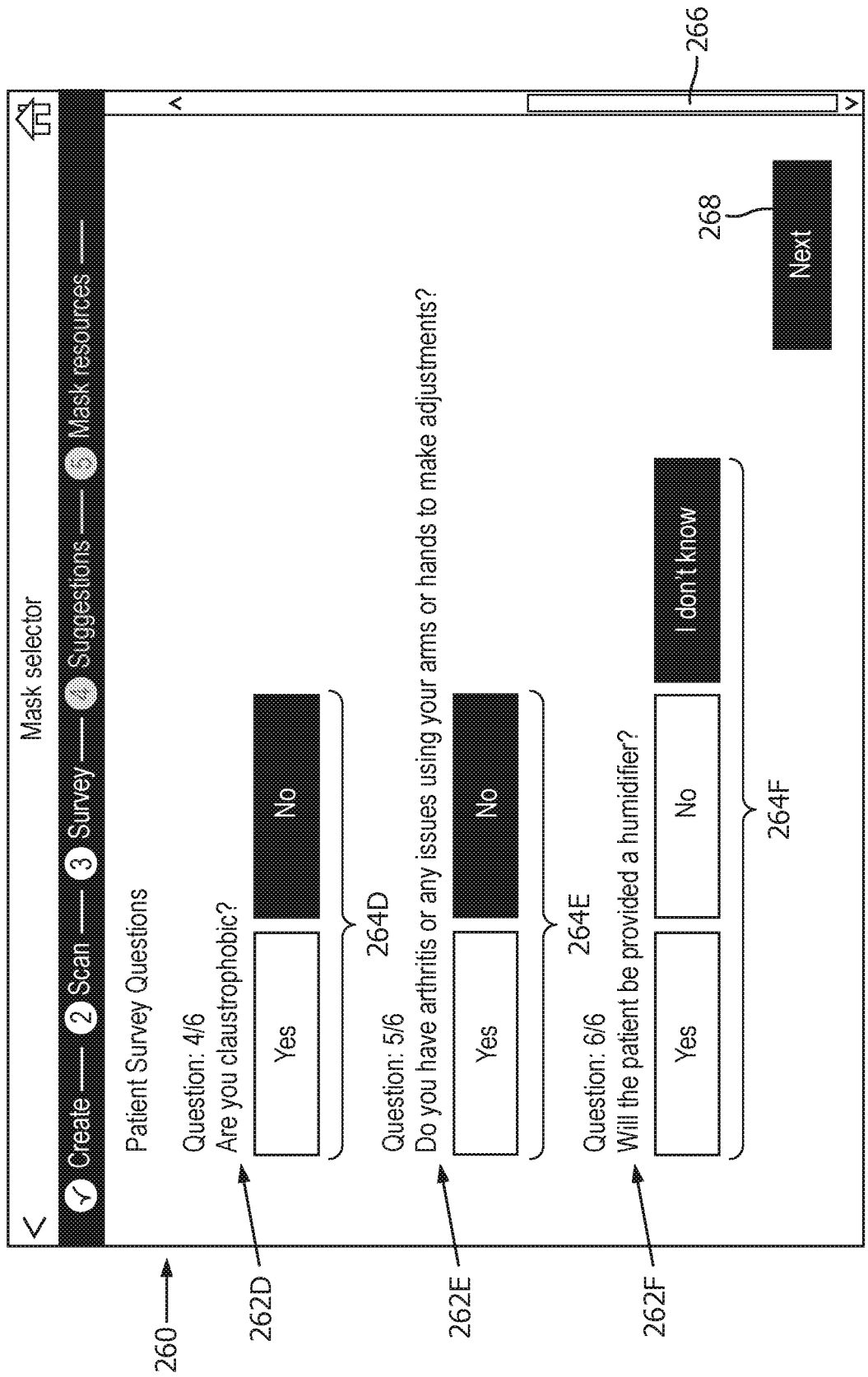
Figure 32:
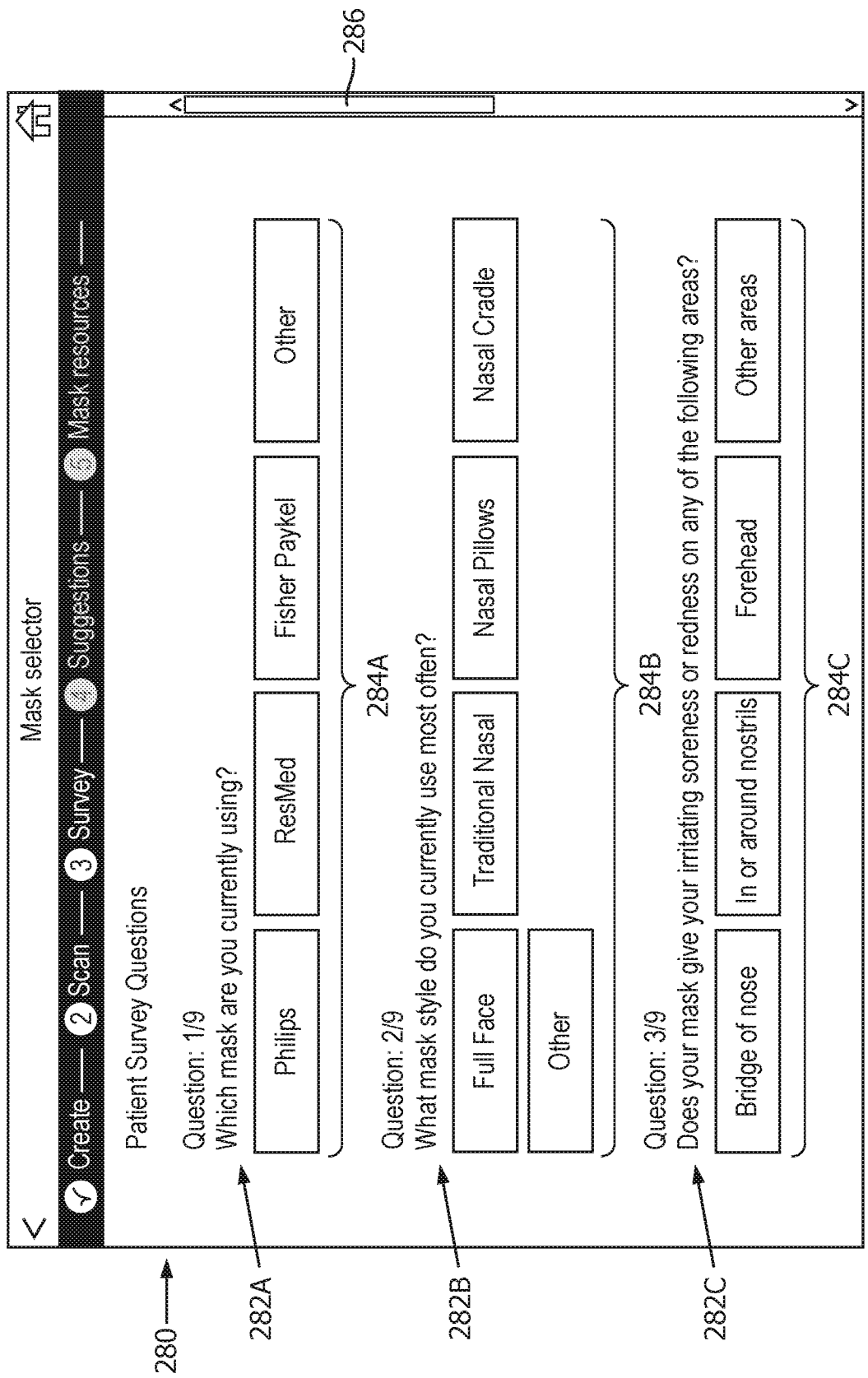
Figure 34:
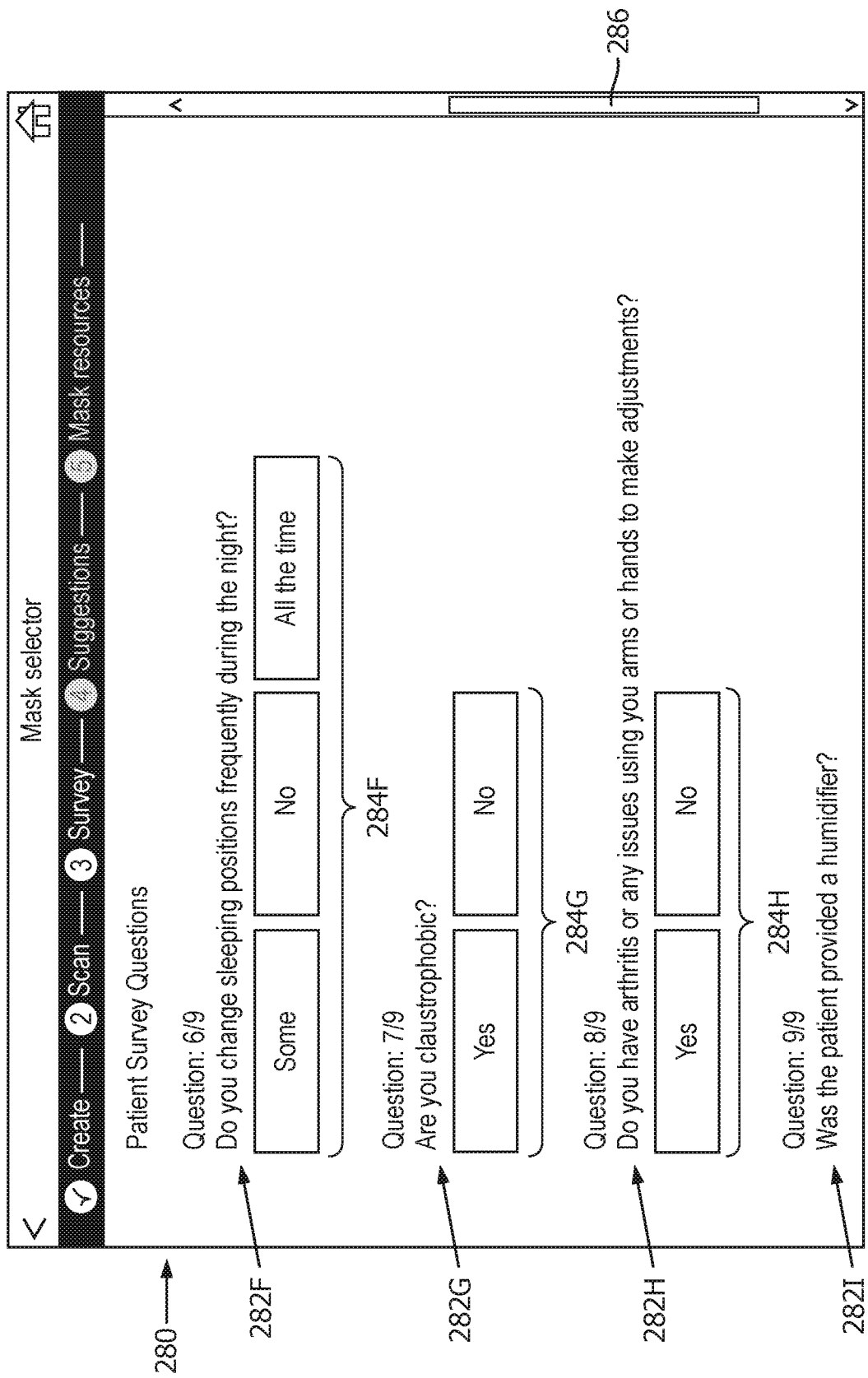
Figure 35:
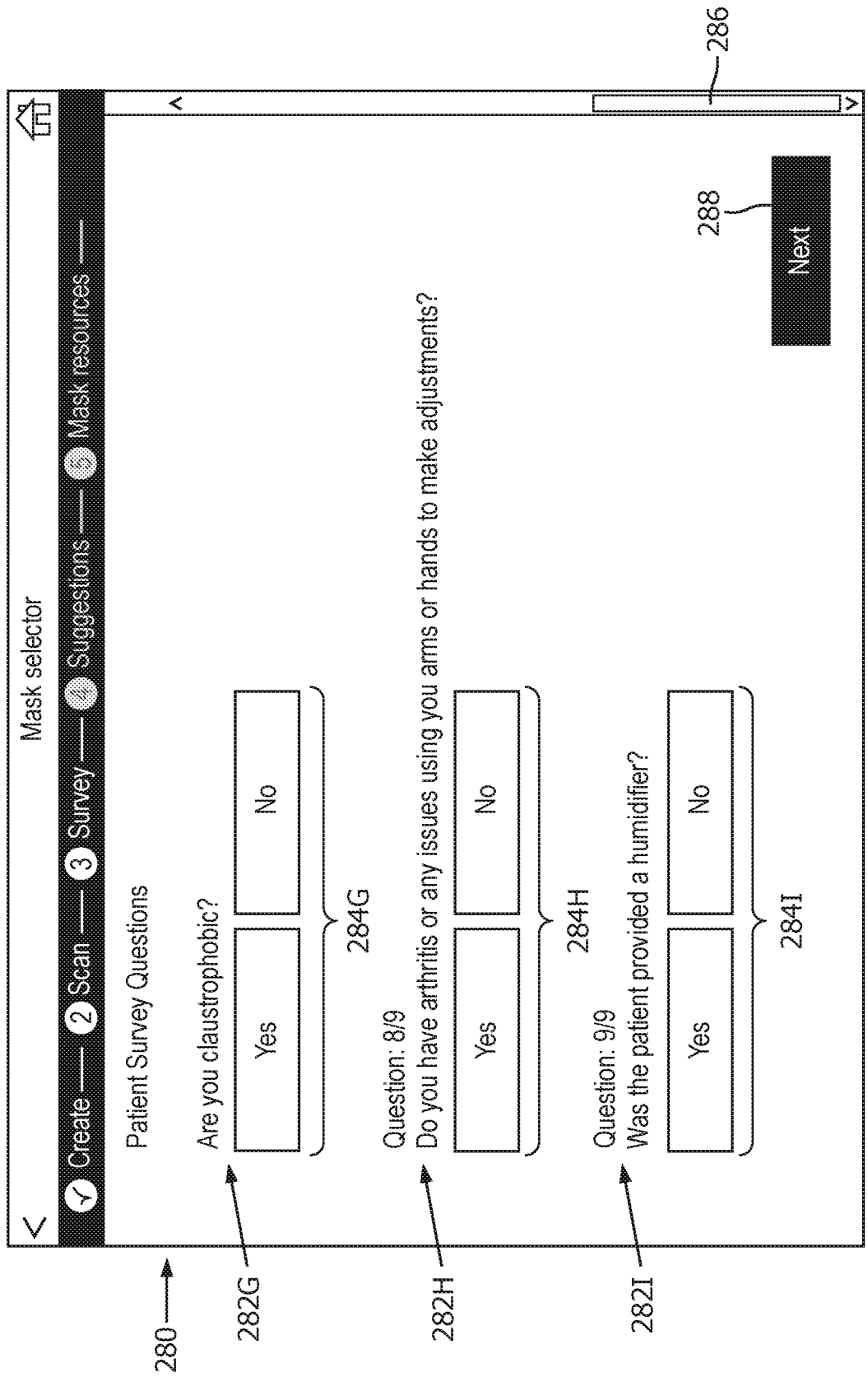

Upon detecting selection of "Next" button 250 of scanning screen 220, software application/tool 41 will cause one of a first patient survey screen 260 (such as shown in FIGS. 30 and 31) or a second patient survey screen 280 (such as shown in FIGS. 32-35) to be displayed on display 26 depending on whether the patient is not, or is, a compliant patient based on the input provided on create patient page 160 as previously discussed.

If the patient is not a compliant patient (i.e., not currently a CPAP mask user as previously indicated on create patient page 160), software application causes first patient survey screen 260 to be displayed on display 26. As shown in FIGS. 30 and 31, first patient survey screen 260 provides a number of questions 262 (six questions 262A-262F are shown in the example shown in FIGS. 29 and 30) along with multiple choice response buttons 264A-264F via which responses may be provided by the patient. Such questions generally enable software application/tool 41 to determine which mask family is best for the patient based on the core feature sets of the mask family. Depending on the quantity of questions displayed on first patient survey screen 260, a scroll bar 266 may be provided to allow for the patient to scroll through the displayed questions 262A-262F. After questions 262A-262F have been answered, the patient may select a "Next" button 268 provided on first patient survey screen 260 to cause software application/tool 41 to process the responses selected by the patient and to use such responses to narrow the pool of potential masks in consideration for the patient. For example, if the patient provides a response 264A to question 262A that indicates that the patient has trouble breathing through their nose, all or certain nasal masks would be downgraded within, or eliminated from, the pool of potential masks in consideration for the patient. In contrast, if the patient provides a response 264A indicative that they do not have any trouble breathing through their nose, nasal masks would be upgraded or particularly included in the pool. As another example, depending on the response 264D provided to question 262D regarding claustrophobia, masks that encroach more or less on a patient's face may be included or removed from the pool of potential masks in consideration for the patient.

If the patient is a compliant patient (i.e., currently a CPAP mask user as previously indicated on create patient page 160), software application/tool 41 causes second patient survey screen 280 to be displayed on display 26. As shown in FIGS. 32-35, second patient survey screen 280 provides a number of questions 282 (nine questions 282A-282I are shown in the example shown in FIGS. 32-35) along with multiple choice response buttons 284A-284I via which responses may be provided by the patient. As these questions are being presented to a patient who is already a mask user and thus is apparently looking to changes masks for one reason or another, such questions are generally intended to identify shortcomings of their present mask and/or areas for improvement. Depending on the quantity of questions displayed on second patient survey screen 280, a scroll bar 286 may be provided to allow for the patient to scroll through the displayed questions 282A-282I. After questions 282A-282I have been answered, the patient may select a "Next" button 288 provided on second patient survey screen 280 to cause software application/tool 41 to process the responses selected by the patient and to use such responses to narrow the pool of potential masks in consideration for the patient.

Figure 36:
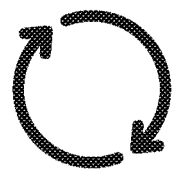
Figure 37:
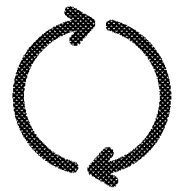

Upon selection of either of "Next" buttons 268 or 288, software application/tool 41 processes the facial images captured during the scanning operation previously described in conjunction with FIGS. 18-29 to create a 3D model of the patient's face/head and utilizes such model, along with the responses provided by the patient on either of first or second patient survey screens 260 or 280 to determine an ordered list of recommended masks for the patient. During such processing, software application/tool 41 may cause one or more of a processing screen 300 (FIG. 36) and/or a calculating screen 310 (FIG. 37) to be displayed on display 26, providing an indication to the user that software application/tool 41 is working to determine masks for the patient.

Figure 38:
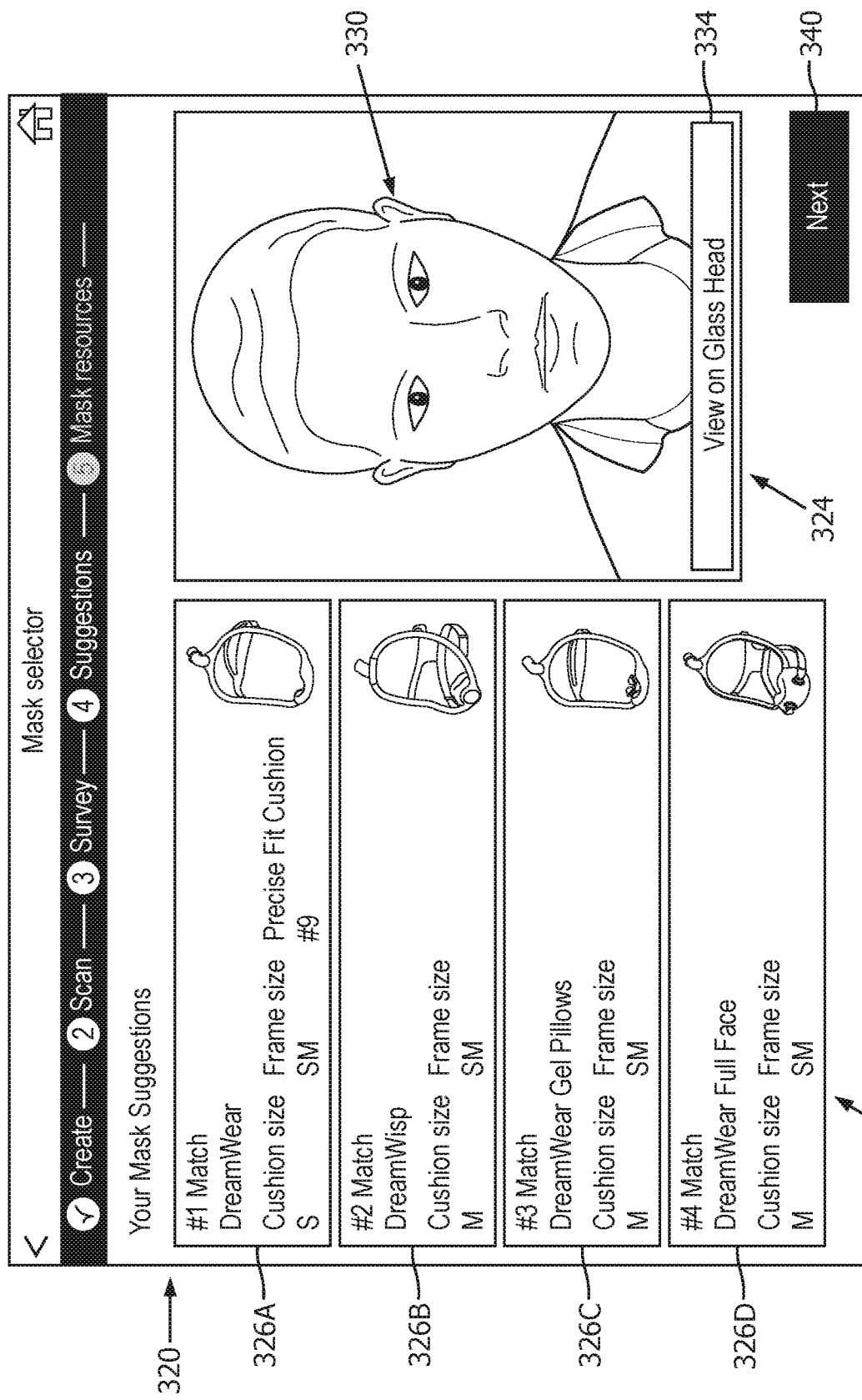
Figure 39:
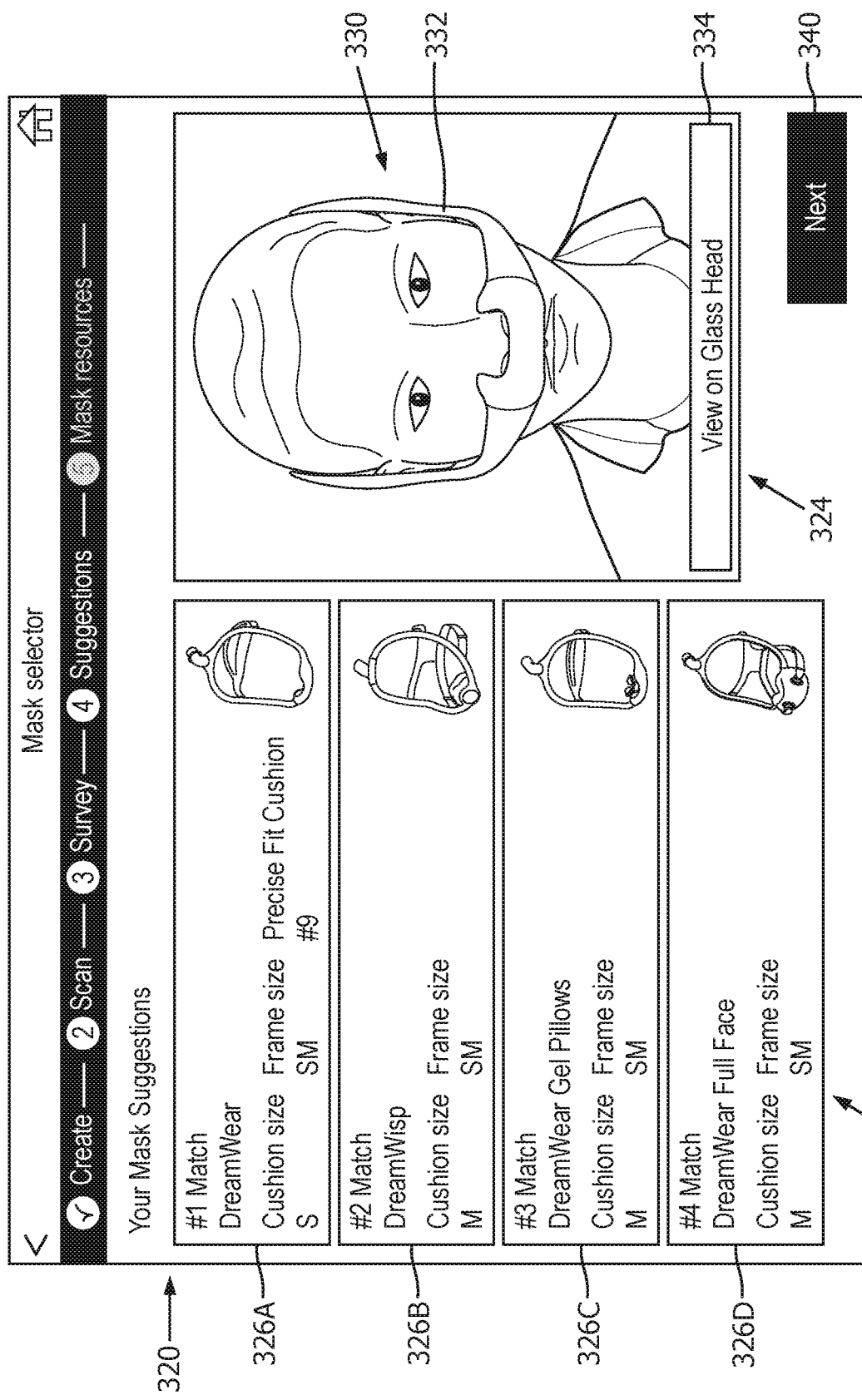
Figure 40:
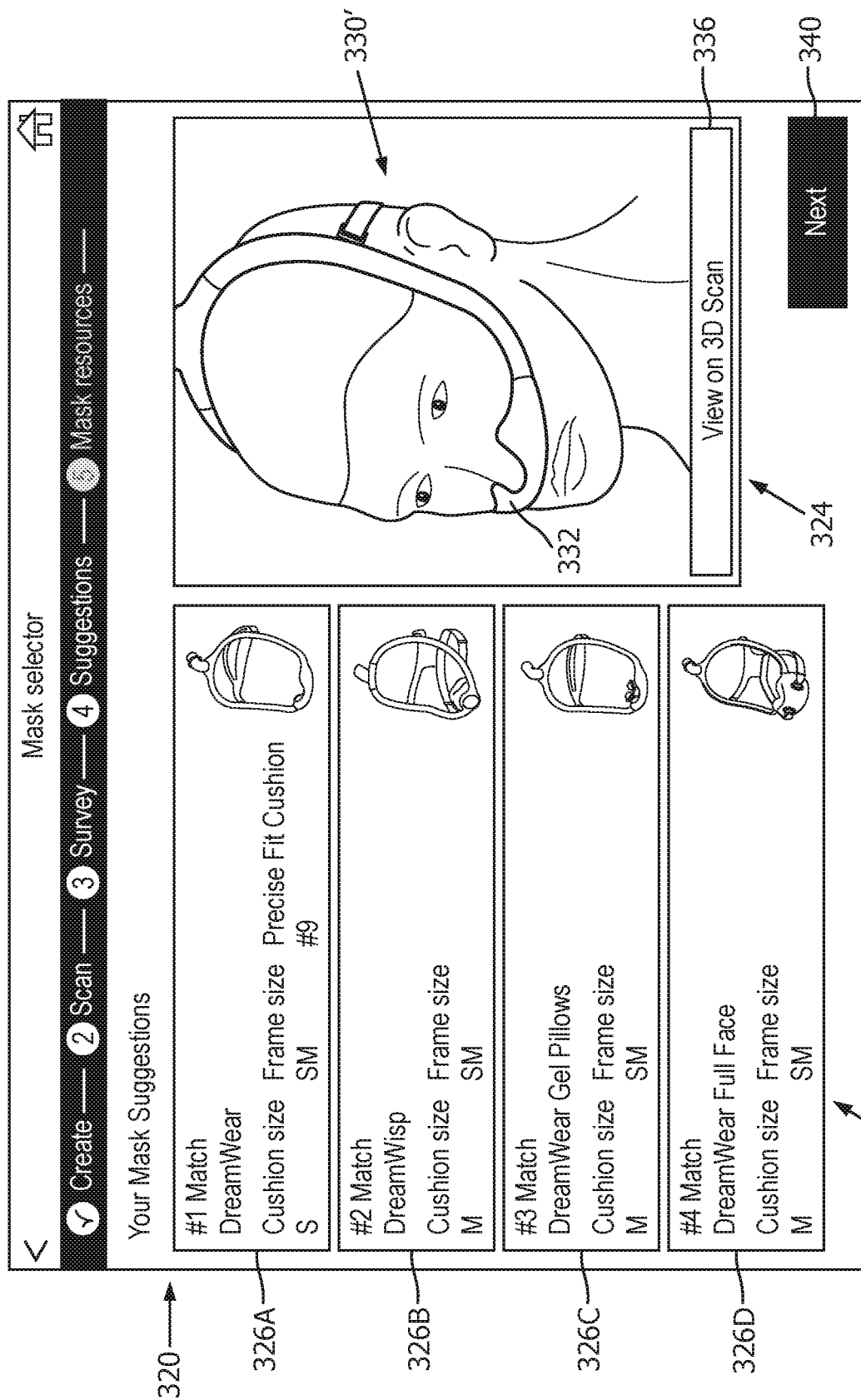

Once software application/tool 41 has completed such processing, software application/tool 41 causes a mask suggestion screen 320 to be displayed on display 26, such as shown in FIGS. 38-40. Mask suggestion screen 320 includes a mask listing portion 322 and a display portion 324.

Mask suggestion portion 324 of mask suggestion screen 320 includes a ranked selectable listing of different masks and sizing details thereof determined to be a best fit for the patient based on potential masks available (e.g., those indicated on Settings screen 132 previously discussed), dimensional information (e.g., geometries, dimensions, etc.) of the potential masks available, the facial geometries of the patient determined from the scanning operation, and the patient responses previously discussed. Such listing may also include an image of each mask. In the example shown in FIGS. 38-40, mask suggestion portion includes four different user selectable mask suggestions 326A-326D, however, it is to be appreciated that the quantity of mask suggestions provided may vary without varying from the scope of the present concept.

Display portion 324 of mask suggestion screen 320 includes a shaded 3D model 330 of the patient's face/head determined from the images captured during the scanning process. In the example shown in FIG. 38, images captured by depth camera 32 were utilized to determine the 3D model itself, while images captured by rear camera 30 were utilized to provide surface texture/coloring to shaded 3D model 330. 3D model 330 may be freely rotated upon selection by a user in order to view model 330 from various angles or sides. As shown in FIG. 39, software application/tool 41 will further provide a 3D mask image 332 of a particular mask arrangement from listing portion 322 upon selection thereof by a user. In the example shown in FIG. 39, the "#1 Match", mask suggestion 326A was selected and thus mask image 332 thereof is displayed on 3D model 330. As an alternative to shaded 3D model 330, a user may select a "View on Glass Head" button 334 provided on mask suggestion screen 320. Upon selection of "View on Glass Head" button 334, software application/tool 41 changes the appearance of 3D model 330 from a shaded appearance to a glass-like 3D model 330', such as shown in FIG. 40 which is rotatable similar to shaded 3D model 330. Upon such change, "View on Glass Head" button 334 is replaced with a "View on 3D Scan" button 336 which may be selected to return back to shaded 3D model 330 from glass-like 3D model 330', as is also shown in FIG. 40. In addition to displaying the selected mask on 3D model 330 or 330', a "Next" button 340 provided on mask suggestion screen 320 becomes selectable upon selection of one of the mask arrangements from listing portion 322, such as shown in FIGS. 39 and 40.

Figure 41:
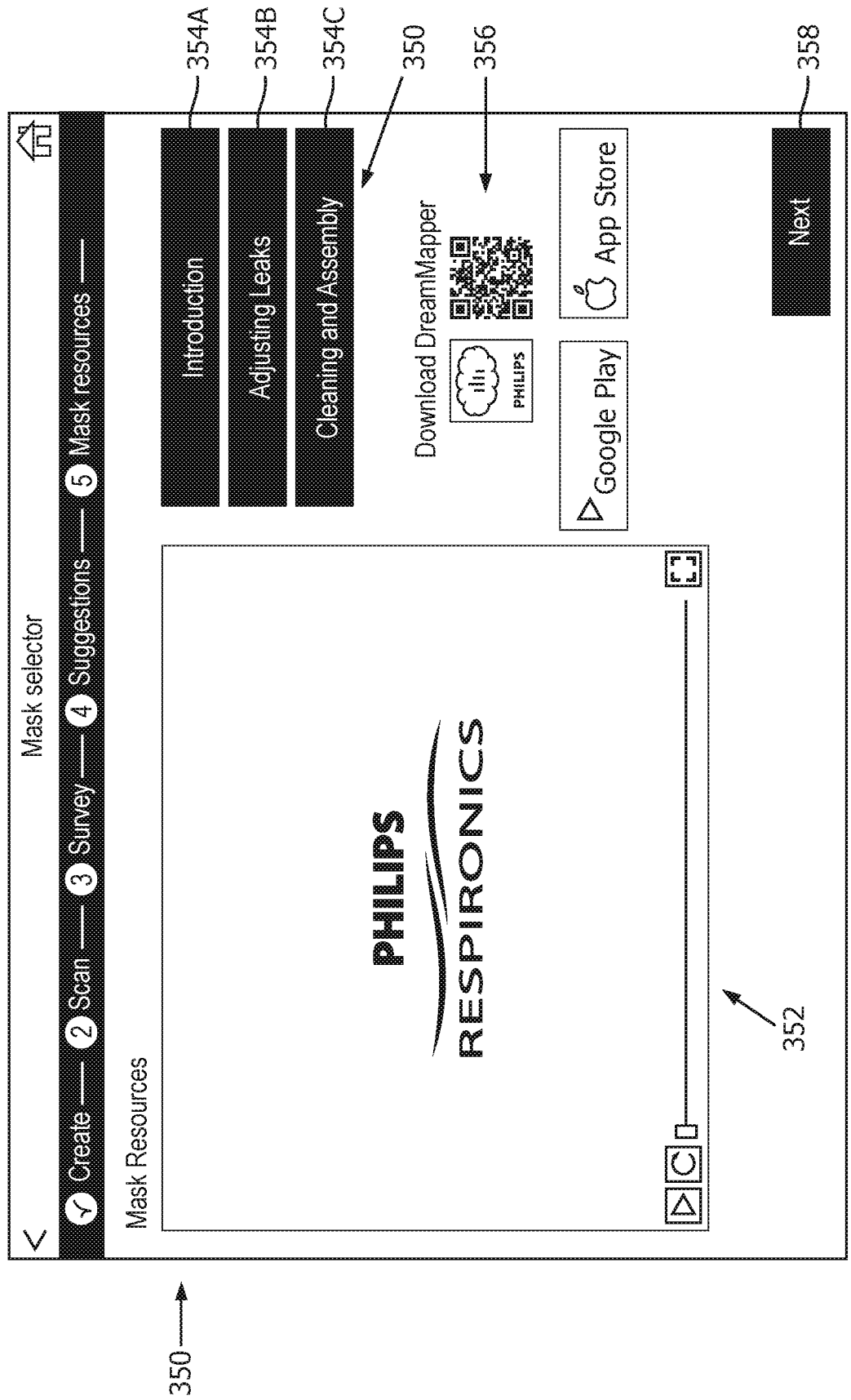

Upon detecting selection of "Next" button 340, software application/tool 41 causes a mask resources screen 350 to be displayed on display 26, such as shown in FIG. 41. The displayed mask resources screen 350 of software application/tool 41 is designed to provide education to the patient regarding the mask previously selected on mask suggestion screen 320. Accordingly, in a first section of mask resources screen 350, a video screen 352 is provided for showing instructional videos regarding information/details of the selected mask and usage thereof to the patient. A plurality of selectable buttons (three buttons 354A-354C are shown in the example embodiment of FIG. 40) are provided in another section 354 of mask resources screen 350 that the user may select in order to cause videos of different topics (e.g., without limitation, introduction to the new mask, adjusting to minimize leaks, cleaning and assembly, etc.) to be displayed on video screen 352. The videos provided may be updated/changed dynamically (i.e., the content may be dynamically updated). One or more links 356 for accessing and/or downloading other applications or materials which may be beneficial to the patient may also be provided on mask resources screen 350. A selectable "Next" button 358 may be provided to allow for a user to proceed past mask resources screen 350.

Figure 42:
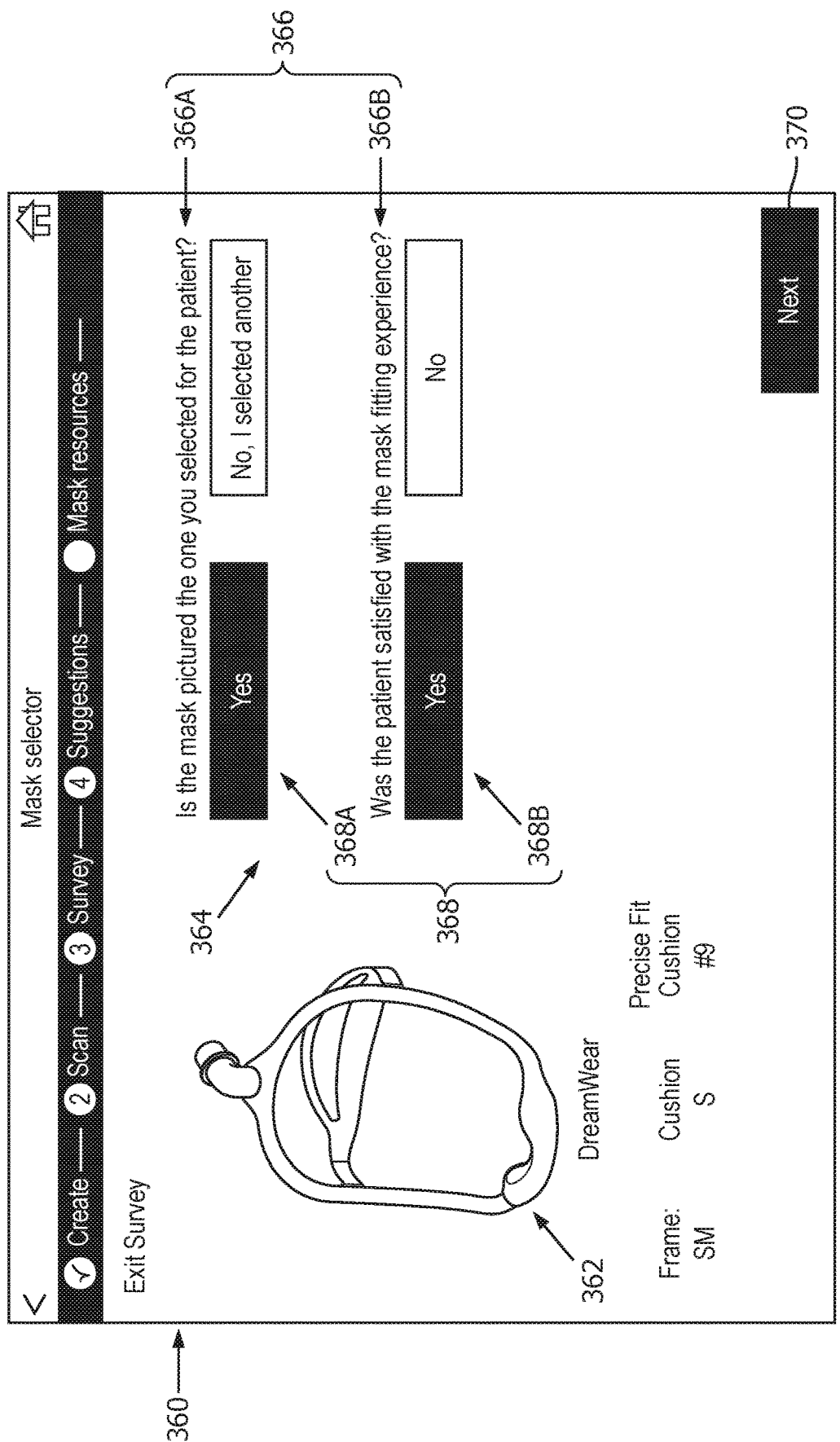
Figure 43:
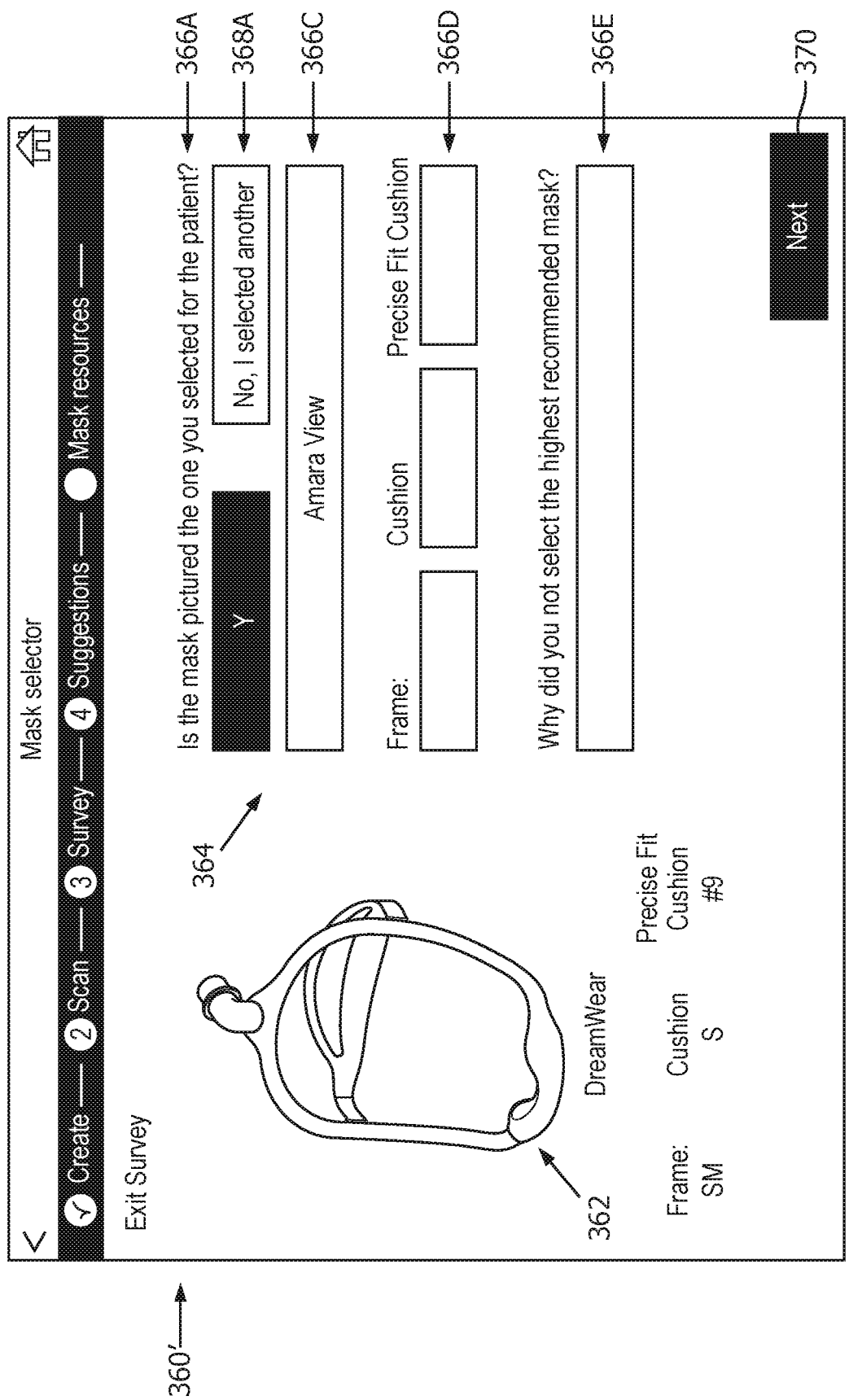

Upon detecting selection of "Next" button 358, software application/tool 41 causes an exit survey screen 360 to be displayed on display 26, such as shown in FIG. 42. In the example shown in FIG. 42, exit survey screen 360 includes a first area 362 in which information pertaining to the mask previously selected on mask suggestion screen 320 is provided. Such information may include, for example, without limitation, one or more images of the selected mask, the name of the selected mask, and sizing information of the selected mask. Exit survey screen 360 includes a second area 364 in which questions 366 are provided along with multiple choice response buttons 368 via which responses may be provided by the user. The quantity and/or content of the questions provided in second area 364 may vary depending on the answers provided. For example, in FIG. 42 a first question 366A "Is the mask pictured the one you selected for the patient?" was answered "Yes", as indicated by the shaded response button of response buttons 368A. In response a "Yes" response to first question 366A, software application/tool 41 provided as a follow-up question the further question 366B "Was the patient satisfied with the mask fitting experience?", which was also answered "Yes". In contrast, in the example exit survey screen 360' shown in FIG. 43, first question 366A was answered "No", as indicated by the shaded response button of response buttons 368A. In response a "No" response to first question 366A, software application/tool 41 provided as a follow-up question the further response questions/requests for input 366C-366E prompting the user to indicate: the name of the mask selected (e.g., from a dropdown menu 366C of masks), details of components of the mask selected at 366C (e.g., the frame, cushion, and precise fit cushion), and information as to why the mask selected was not the highest recommended mask. Such information may be used for analytics purposes (e.g., to check for consistency across clinicians), for market information, or for identifying possible problems or errors in software application/tool 41 or in the use thereof. A selectable "Next" button 370 may be provided to allow for a user to proceed past exit survey screens 360, 360' after providing the information requested therein.

Figure 44:
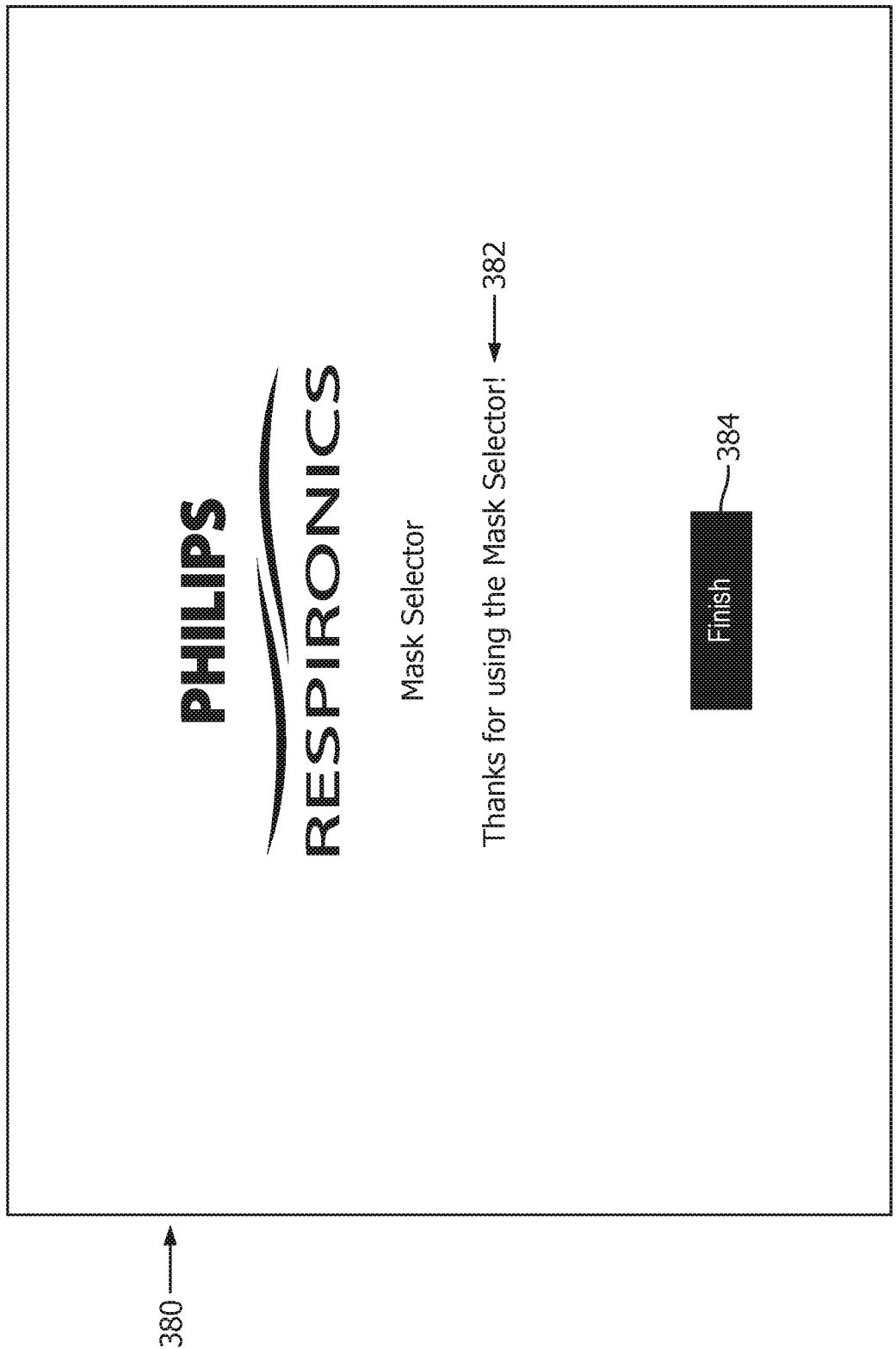

Upon detecting selection of "Next" button 370, software application/tool 41 causes a finish screen 380 to be displayed on display 26, such as shown in FIG. 44. In the example shown in FIG. 44, finish screen 380 includes a farewell message 382 "Thanks for using the Mask Selector!" along with a selectable "Finish" button 384. Upon detecting selection of "Finish" button 384, software application/tool 41 will once again cause login screen 60 to be displayed on display 26. In another example embodiment, upon detecting selection of "Finish" button 384, software application/tool 41 will close and the user will be returned to viewing whatever they were previously viewing on display 26 prior to using software application/tool 41. In an example embodiments of the present invention, the patient is provided with the selected mask when still using, or upon completing use of software application/tool 41, however, it is to be appreciated that the patient may be provided with such mask or otherwise obtain such mask at a later time without varying from the scope of the present invention.

From the foregoing description it will readily be appreciated that the majority of the data collected and stored in carrying out the arrangements described herein is private and sensitive user information and thus must be safeguarded from potential disclosure to, or discovery by, potential third parties. Such private and sensitive user information that is available during scanning includes facial scans, depth map data, information about user (e.g., metadata including age, bmi etc.), mask recommendations, etc. There are known methods used today that may be employed to safeguard the private and sensitive information and it remains with the central database. Even though the central database is safeguarded with access rights and protection, there are chances that the data residing with the database could be compromised. Hence, an intelligent and smart workflow has been crafted to safeguard the personal and sensitive user information and at the same time provide access to users/services which require access to this data.

In one example embodiment of the present invention an advanced Asymmetric Cryptography technique using Public and Private keys to secure the client/server nodes in the architecture has been employed. In such arrangement, clients and authorized users have their own dedicated public keys that are secured using an AES (Advanced Encryption System) symmetric hash. The private keys are created for every scan and are packed together with the public key and saved in the central database. The webservices contain their own public key and can process/access information as appropriate through key exchange. Public keys may also be created for particular users in order to provide access to information from the scans for specific research purposes. Such users are allowed to access the data through a proprietary application with restricted access granularities. Some advantages of such arrangement are: the private sensitive data can be kept securely in the cloud central database and the client systems/webservices can use them as required for processing or extracting any information as required; if there is any potential breach/security threat, which causes the client systems to be compromised, without the private key (which is available in the cloud server) no information can be extracted/leaked from the central database.

The main element(s) of the arrangement include an encryption engine that resides in the client and the server application. The encryption engine creates the private key for the clients whenever new scans are created. During the scan creation, the server also creates a private key of the scan and stores it in the database. The private key of the scan is masked with a transparent public key and encrypted using an asymmetric cryptosystem. The public and private key combination is sent to the cloud database. The webservices have their own private key that is used for processing the scans as appropriate. The private key-public key decryption takes place as a token exchange between the webservice and a cloud server application layer. The webservices are limited to the data that they can access based on their application and usage. Once the data is processed, the results (non-private information) can be sent back to the client systems and the derived information (including parametric coefficients, any other sensitive information) can be stored with the scans in the database with their corresponding private/public key hash. If access to the information for any research purposes is needed, a separate public key which is provided only for people with proper user access may be utilized to access the data through one or more proprietary applications that does not allow data export/stealing.

It is contemplated that aspects of the disclosed concept can be embodied as computer readable codes on a tangible computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of identifying a particular mask for a patient for use in delivering a flow of breathing gas to the patient, the method comprising:
   capturing with a visual presentation and interaction component a plurality of images of the patient;
   determining a location from which the plurality of images were captured;
   eliminating one or more masks from a pool of potential masks for the patient to create a reduced pool of potential masks based on at least one mask preference associated with the location from which the plurality of images were captured;

constructing a 3D model of a portion of the patient from a number of the plurality of images of the patient;

utilizing the 3D model to determine the particular mask for the patient from the reduced pool of potential masks; and identifying the particular mask to the patient via the visual presentation and interaction component.

2. The method of claim 1, wherein the plurality of images are captured while someone other than the patient is operating the visual presentation and interaction component.

3. The method of claim 1, wherein the plurality of images are captured while the patient is operating the visual presentation and interaction component.

4. The method of claim 1, wherein the visual presentation and interaction component comprises a tablet PC or a smartphone.

5. The method of claim 1, further comprising displaying the plurality of images in an image display area on a display of the visual presentation and interaction component as the plurality of images are captured.

6. The method of claim 5, further comprising displaying an indicator in the image display area for assisting in positioning the patient in the plurality of images.

7. The method of claim 6, wherein displaying the indicator further comprises displaying the indicator in different colors to provide different indications to a person using the visual presentation and interaction component while capturing the plurality of images.

8. The method of claim 6, wherein displaying the indicator further comprises displaying a directional indicator instructing a person using the visual presentation and interaction component while capturing the plurality of images to move one of the visual presentation and interaction component in a particular direction or for the patient to move in a particular direction.

9. The method of claim 1, wherein identifying the mask to the patient comprises displaying information regarding the particular mask on a display of the visual presentation and interaction component.

10. The method of claim 9, wherein the information comprises a name and size of the particular mask or one or more components of the particular mask.

11. The method of claim 1, wherein utilizing the 3D model to determine the particular mask for the patient from the reduced pool of potential masks comprises mapping three dimensional representations of the masks from the reduced pool of potential masks to the 3D model.

12. The method of claim 1, wherein determining the location from which the plurality of images were captured comprises determining one or more of: an address, a zip code, a city, a state, and/or a country.

13. The method of claim 1, wherein identifying the particular mask to the patient via the visual presentation and interaction component comprises displaying a ranked listing of masks including the particular mask.

14. A system configured to identify a particular mask for a patient for use in delivering a flow of breathing gas to the patient, the system comprising:

a visual presentation and interaction component including a display; and a processor apparatus including a processor and a memory, the memory storing one or more routines executable by the processor, the one or more routines being adapted to:

capture, with the visual presentation and interaction component, a plurality of images of the patient;

determine a location from which the plurality of images were captured;

eliminate one or more masks from a pool of potential masks for the patient to create a reduced pool of potential masks based on at least one mask preference associated with the location from which the plurality of images were captured;

construct a 3D model of a portion of the patient from a number of the plurality of images of the patient;

utilize the 3D model to determine the particular mask for the patient from the reduced pool of potential masks; and identify the particular mask to the patient via the display.

15. The system of claim 14, wherein the visual presentation and interaction component comprises a tablet PC or a smartphone.

16. The system of claim 14, wherein the one or more routines are further adapted to display the plurality of images in an image display area on the display of the visual presentation and interaction component as the plurality of images are captured.

17. The system of claim 14, wherein the location from which the plurality of images were captured comprises one or more of: an address, a zip code, a city, a state, and/or a country.

18. The system of claim 14, wherein the one or more routines are adapted to identify the particular mask to the patient via the display in a ranked listing of masks including the particular mask.

19. A non-transitory computer readable medium storing one or more programs, including instructions, which when executed by a computer, causes the computer to perform a method of identifying a particular mask for a patient for use in delivering a flow of breathing gas to the patient, the method comprising:

capturing with a visual presentation and interaction component a plurality of images of the patient;

determining a location from which the plurality of images were captured;

eliminating one or more masks from a pool of potential masks for the patient to create a reduced pool of potential masks based on at least one mask preference associated with the location from which the plurality of images were captured;

constructing a 3D model of a portion of the patient from a number of the plurality of images of the patient;

utilizing the 3D model to determine the particular mask for the patient from the reduced pool of potential masks; and identifying the particular mask to the patient.

* * * * *